United States Patent [19]

Marks et al.

[11] Patent Number: 5,175,191
[45] Date of Patent: Dec. 29, 1992

[54] POTENT INDUCERS OF TERMINAL DIFFERENTIATION AND METHODS OF USE THEREOF

[75] Inventors: Paul A. Marks, Bridgewater, Conn.; Richard A. Rifkind, New York, N.Y.; Ronald Breslow, Englewood, N.J.; Branko Jursic, New York, N.Y.

[73] Assignees: Sloan-Kettering Institute for Cancer Research; The Trustees of Columbia University Institute for Cancer Research in the City of New York, both of New York, N.Y.

[21] Appl. No.: 522,558

[22] Filed: May 14, 1990

Related U.S. Application Data

[63] Continuation-in-part of Ser. No. 374,343, Jun. 30, 1989, Pat. No. 5,055,608, which is a continuation-in-part of Ser. No. 270,963, Nov. 14, 1988, abandoned.

[30] Foreign Application Priority Data

Nov. 14, 1989 [WO] World Int. Prop. O. .................. PCT/US89/05203

[51] Int. Cl.⁵ .................. A61K 31/185; C07C 259/10
[52] U.S. Cl. .................. 514/575; 562/621; 562/622
[58] Field of Search .................. 562/621, 622, 623; 564/160; 514/575

[56] References Cited

FOREIGN PATENT DOCUMENTS 46-08683  5/1971  Japan .................. 514/575

OTHER PUBLICATIONS

Hynes, John B. "Hydroxylamine derivatives as potential antimalarial agents" CA 74:22521a, 1971.

*Primary Examiner*—Richard L. Raymond
*Assistant Examiner*—Brian Bembenick
*Attorney, Agent, or Firm*—John P. White; Craig J. Arnold

[57] ABSTRACT

The invention provides compounds, several of which belong to a class having two or more nonpolar components connected by a polar group and having polar groups on the termini of the compound.

The invention also concerns a method of selectively inducing termini differentiation of neoplastic cells and thereby inhibiting proliferation of such cells which comprises contacting the cells under suitable condition with an amount of the compound effect to selectively induce terminal differentiation.

Moreover, the invention provides a method of treating a patient having a tumor characterized by proliferation of neoplastic cells which comprises administering to the patient an amount of the compound effective to selectively induce terminal differentiation of such neoplastic cells, thereby inhibiting their proliferation and suppressing oncogenicity.

Lastly, the present invention provides a pharmaceutical composition comprising a pharmaceutically acceptable carrier and the compound in an amount effective less than an amount which would cause toxicity in the patient.

3 Claims, 11 Drawing Sheets

Figure 3A

| Conc. of IC-135 (mM) | Cell Count (millions) | B+ cells |
|---|---|---|
| 1 | 2.4 | 68-69 |
| 2 | 1.9 | 77-80 |
| 3 | 1.2 | 78-81 |
| 4 | 0.5 | 3-4 |
| 5 | 0.2 | 0-1 |

Control cell ⟶ 0-1

5mM HMBA ⟶ 89-88

POTENT INDUCERS OF TERMINAL DIFFERENTIATION AND METHODS OF USE THEREOF

This is a continuation-in-part application of U.S. Ser. No. 374,343, filed Jun. 30, 1989, (now U.S. Pat. No. 5,055,608) which in turn is a continuation-in-part of application U.S. Ser. No. 270,963, filed Nov. 14, 1988, (abandoned) the contents of which are hereby incorporated by reference into the present application.

BACKGROUND OF THE INVENTION

Throughout this application various publications are referenced by arabic numerals within parentheses. Full citations for these publications may be found at the end of the specification immediately preceding the claims. The disclosures of these publications in their entireties are hereby incorporated by reference into this application in order to more fully describe the state of the art to which this invention pertains.

Cancer is a disorder in which a population of cells has become, in varying degrees, unresponsive to the control mechanisms which normally govern proliferation and differentiation. For many years there have been two principal strategies for chemotherapeutic treatment of cancer: a) blocking hormone-dependent tumor cell proliferation by interference with the production or peripheral action of sex hormones; and b) killing cancer cells directly by exposing them to cytotoxic substances, which injure both neoplastic and normal cell populations.

Relatively recently, cancer therapy is also being attempted by the induction of terminal differentiation of the neoplastic cells (1). In cell culture models differentiation has been reported by exposure of cells to a variety of stimuli, including: cyclic AMP and retinoic acid (2,3), aclarubicin and other anthracyclines (4).

There is abundant evidence that neoplastic transformation does not necessarily destroy the potential of cancer cells to differentiate (1,5,6). There are many examples of tumor cells which do not respond to the normal regulators of proliferation and appear to be blocked in the expression of their differentiation program, and yet can be induced to differentiate and cease replicating. A variety of agents, including some relatively simple polar compounds (5,7-9), derivatives of vitamin D and retinoic acid (10-12), steroid hormones (13), growth factors (6,14), proteases (15,16), tumor promoters (17,18), and inhibitors of DNA or RNA synthesis (4,19-24), can induce various transformed cell lines and primary human tumor explants to express more differentiated characteristics.

Early studies by the present inventors identified a series of polar compounds that were effective inducers of differentiation in a number of transformed cell lines (8,9). Of these, the most effective inducer, until recently, was the hybrid polar/apolar compound N,N'-hexamethylene bisacetamide (HMBA) (9). The use of polar/apolar compounds to induce murine erythroleukemia cells (MELC) to undergo erythroid differentiation with suppression of oncogenicity has proved a useful model to study inducer-mediated differentiation of transformed cells (5,7-9). HMBA-induced MELC terminal erythroid differentiation is a multistep process. Upon addition of HMBA to MELC (745A-DS19) in culture, there is a latent period of 10 to 12 hours before commitment to terminal differentiation is detected. Commitment is defined as the capacity of cells to express terminal differentiation despite removal of inducer (25). Upon continued exposure to HMBA there is progressive recruitment of cells to differentiate. Recently, the present inventors reported that MELC cell lines made resistant to relatively low levels of vincristine become markedly more sensitive to the inducing action of HMBA and can be induced to differentiate with little or no latent period (26).

HMBA is capable of inducing phenotypic changes consistent with differentiation in a broad variety of cells lines (5). The characteristics of the drug induced effect have been most extensively studied in the murine erythroleukemia cell system (MELC) (5,25,27,28). MELC induction of differentiation is both time and concentration dependent. The minimum concentration required to demonstrate an effect in vitro in most strains is 2 to 3 mM; the minimum duration of continuous exposure generally required to induce differentiation in a substantial portion (>20%) of the population without continuing drug exposure is about 36 hours.

The primary target of action of HMBA is not known. There is evidence that protein kinase C is involved in the pathway of inducer-mediated differentiation (29). The in vitro studies provided a basis for evaluating the potential of HMBA as a cytodifferentiation agent in the treatment of human cancers (30). Several phase I clinical trials with HMBA have been completed (31-36). Recently, the first evidence was reported that this compound can induce a therapeutic response in patients with cancer (35,36). These phase I clinical trials demonstrate that the potential efficacy of HMBA is limited, in part, by dose-related toxicity which prevents achieving optimal blood levels and by the need for intravenous administration of large quantities of the agent, over prolonged periods.

The present invention provides new chemical inducers which are 2-20 times more active than HMBA. It has unexpectedly been found that compounds having two or more nonpolar components connected by a polar group and having groups on the termini of the compound are effective inducers of terminal differentiation. For instance, bis-hexamethylene triacetamide, which comprises three acetamide groups connected by two six-carbon chains, has been found to be a potent inducer of terminal differentiation in MELC.

This new class of compounds of the present invention may be useful for selectively inducing terminal differentiation of neoplastic cells and therefore aid in treatment of tumors in patients.

SUMMARY OF THE INVENTION

The invention provides a class of compounds having the structure:

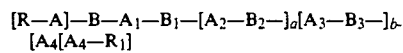

wherein each of A, $A_1$, $A_2$, $A_3$, and $A_4$ represent a polar group which comprises a nitrogen, sulfur or oxygen atom wherein each of A, $A_1$, $A_2$, $A_3$, and $A_4$ may independently be the same as, or different from, the others of A, $A_1$, $A_2$, $A_3$, and $A_4$;

wherein each of R and $R_1$ is a hydrogen atom; a lower alkyl, alkenyl, or alkynyl group; or a group having the structure:

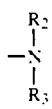

wherein each of $R_2$ and $R_3$ being a hydrogen atom or a lower alkyl, alkenyl, or alkynyl group; and wherein each of R, $R_1$, $R_2$ and $R_3$ may independently be the same as, or different from the other of R, $R_1$, $R_2$ and $R_3$;

wherein each of [R—A] and [$A_4$—$R_1$] have a dipole moment greater than about 2.7 Debye units;

wherein each of B, $B_1$, $B_2$, and $B_3$ represents a nonpolar group which comprises at least 4 atoms in a chain, the termini of which chains are attached to A and $A_1$, $A_1$ and $A_2$, $A_2$ and $A_3$, and $A_3$ and $A_4$, and respectively; wherein each such atom is oxygen, nitrogen, carbon, or sulfur and wherein each of B, $B_1$, $B_2$, and $B_3$ may independently be the same as, or different from the others of B, $B_1$, $B_2$ and $B_3$;

and wherein each of a and b is independently 0 or 1.

Other compounds of this invention include a compound having the structure:

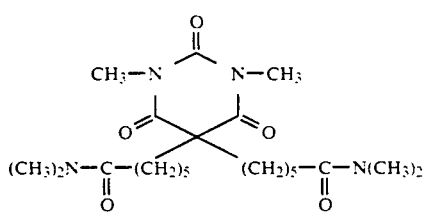

or a compound having the structure:

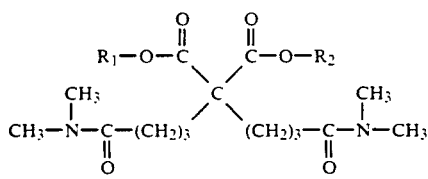

wherein R1 and R2 may be the same or different and each is a lower alkyl group.

Also provided by this invention is a compound having the structure:

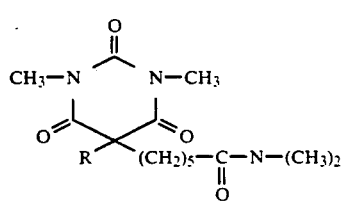

wherein R is H or a lower alkyl group.

This invention further provides a compound having the structure:

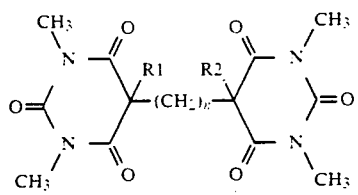

wherein n is an integer which is greater than 1 and $R_1$ and $R_2$ may be the same or different and each is H or a lower alkyl group.

A compound having the structure:

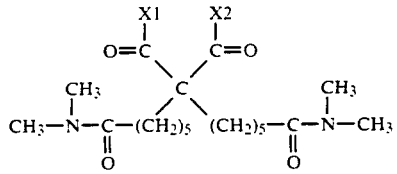

is also provided by this invention wherein X1 and X2 may independently be the same or different and each is $N(CH_3)_2$, NH-phenyl, or $HNCH_3$.

This invention also provides a compound having the structure:

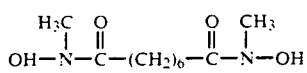

or a compound having the structure:

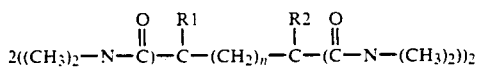

wherein $R_1$ and $R_2$ may be the same or different and each is H or a lower alkyl group and n is an integer from 1 to 10.

This invention further provides a compound having the structure:

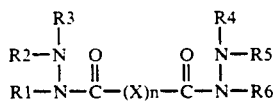

wherein R1, R2, R3, R4, R5, R6 may independently be the same or different from each other and is H or a lower alkyl group; wherein X is methyl or phenyl; and n is an integer from 1 to about 15.

A compound having the structure:

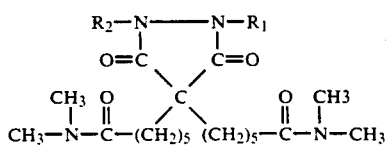

is also provided by this invention wherein R1 and R2 may be the same or different and is H or CH3.

The invention also provided a compound having the structure:

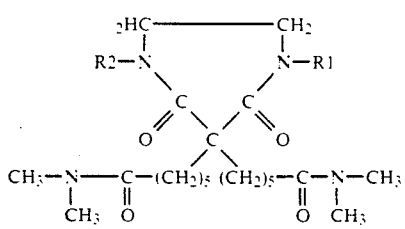

wherein $R_1$ and $R_2$ may be the same or different and is H or $CH_3$.

A compound having the structure:

is provided by this invention, wherein X has the structure:

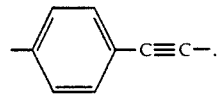

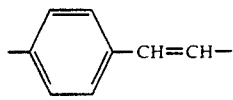

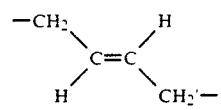

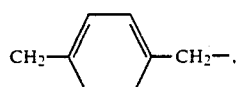

or

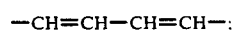

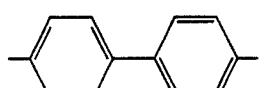

wherein $R_1$ and $R_2$ are the same or different and is H or lower alkyl group.

Further provided by this invention is a compound having the structure:

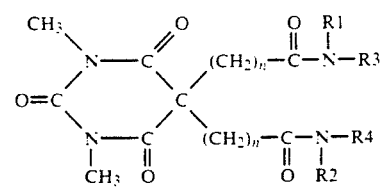

wherein R1 and R1 may independently be the same or different and each may be H or a lower alkyl group; wherein R3 and R4 may independently be the same or different and each may be CH3 or OH; and wherein n is 5 or 6.

A compound having the structure:

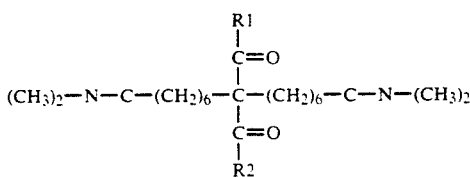

is also provided by this invention, wherein $R_1$ and $R_2$ is the same or different and is hydrogen, lower alkyl, alkenyl, alkynyl, an amide or hydroxyamide.

This invention further provided a compounds having the following structures:

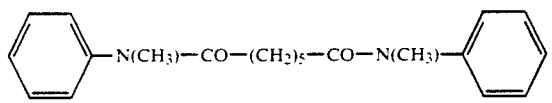

and

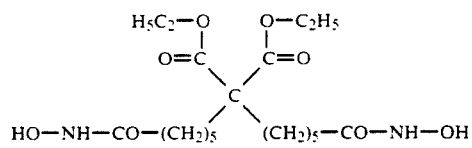

also,

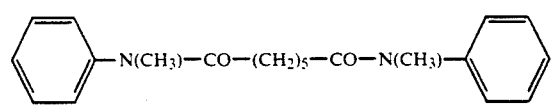

and a compound having the structure:

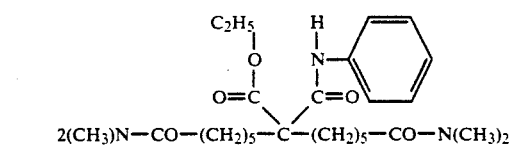

The invention also concerns a method of selectively inducing terminal differentiation of neoplastic cells and thereby inhibiting proliferation of such cells which comprises contacting the cells under suitable condition with an amount of the compound effective to selectively induce terminal differentiation.

Moreover, the invention provides a method of treating a patient having a tumor characterized by proliferation of neoplastic cells which comprises administering to the patient an amount of the compound effective to selectively induce terminal differentiation of such neoplastic cells, thereby inhibiting their proliferation, and suppressing oncogenicity.

Lastly, the present invention provides a pharmaceutical composition comprising a pharmaceutically acceptable carrier, and the compound in an amount less than an amount which cause toxicity in the patient.

DETAILED DESCRIPTION OF THE INVENTION

Figure 1A:
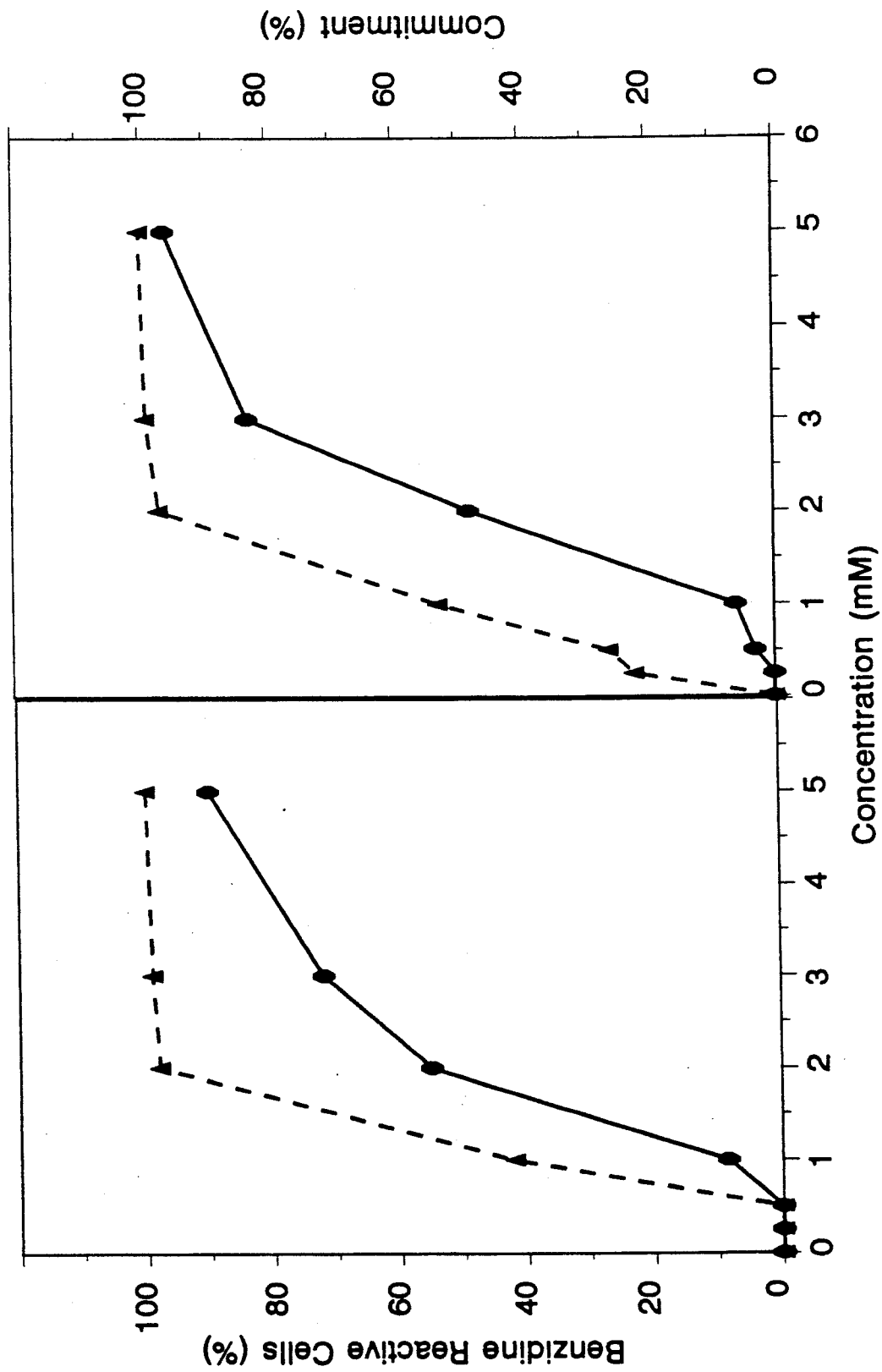
FIG. 1: Comparison of the hybrid polar/apolar compounds, (A) hexamethylene bisacetamide (HMBA); (B) suberic acid bis-N-methyl diacetamide (SBDA); and (C) bis-hexamethylene triacetamide (BHTA) as inducers of differentiation of vincristine-sensitive (745A-DS19) (●) and vincristine-resistant (VCR.C(2) 15) (▲) MELC for HMBA and SBDA and (V3.17) for BHTA. Each compound was added to the cells in culture at the final concentration indicated. Benzidine reactive cells (left panel of each section of this figure) were determined after 4 d. of culture and commitment (right panel of each section of this figure) after 2 d. of culture.
Figure 1B:
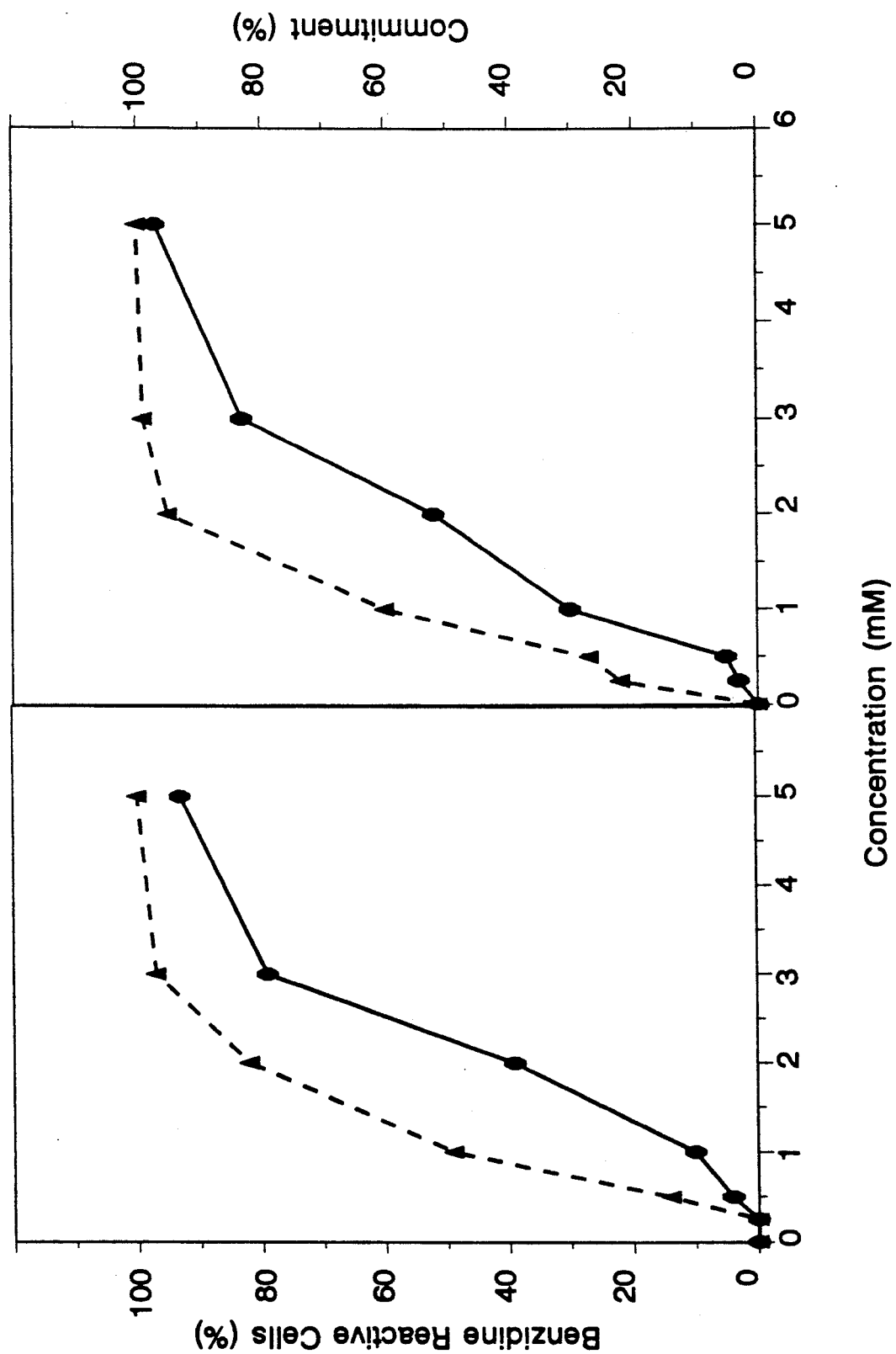

The invention provides a class of compounds having the structure:

[R—A]—B—A$_1$—B$_1$—[A$_2$—B$_2$—]$_a$[A$_3$—B$_3$—]$_b$-[A$_4$—R$_1$]

wherein each A, A$_1$, A$_2$, A$_3$, and A$_4$ represent a polar group which comprises a nitrogen, sulfur or oxygen atom and wherein each of A, A$_1$, A$_2$, A$_3$, and A$_4$ may independently be the same as, or different from, the others of A, A$_1$, A$_2$, A$_3$, and A$_4$;

wherein each of R and R$_1$ is a hydrogen atom; a lower alkyl, alkenyl, or alkynyl group; or a group having the structure:

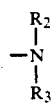

wherein each of R$_2$ and R$_3$ being a hydrogen atom or a lower alkyl, alkenyl, or alkynyl group; and wherein each of R, R$_1$, R$_2$ and R$_3$ may independently be the same as, or different from, the others of R, R$_1$, R$_2$ and R$_3$;

wherein each of [R—A] and [A$_4$—R$_1$] have a dipolar moment greater than about 2.7 Debye units;

wherein each of B, B$_1$, B$_2$, and B$_3$ represents a nonpolar group which comprises at least 4 atoms in a chain, the termini of which chains are attached to A and A$_1$, A$_1$ and A$_2$, A$_2$ and A$_3$, and A$_3$ and A$_4$, respectively;

wherein each such atom is oxygen, nitrogen, carbon, or sulfur and wherein each of B, B$_1$, B$_2$, and B$_3$ may independently be the same as, or different from the others of B, B$_1$, B$_2$, and B$_3$;

and wherein each of a and b is independently 0 or 1.

The compounds of the present invention are made up of two components. One component comprises a polar group, i.e. functional groups with significant dipole moments, such as amides, sulfoxides, amine oxides and related functional groups.

The terminal portions of the compound, represented by R—A and A$_4$—R$_1$, each have dipole moments greater than about 2.7 debye units. The polar groups within the compound, represented by —A$_1$, —A$_2$— and —A$_3$—, have significant dipolar moments but not necessarily in excess of 2.7 debye units. In the preferred embodiments, the polar groups are carbonyl radicals or bivalent radicals of an amide, a sulfoxide or a amine oxide. Each polar group need not necessarily be the same as the other polar groups. In the most preferred embodiments, the poplar groups within the compound are the same as each other and the terminal polar groups are the same. Preferably, all the polar groups are amide groups attached to the compound at the nitrogen atom or at the carbon atom of the carbonyl radical. The amide group may comprise one or more hydrocarbon substituents, such as a lower alkyl or alkenyl groups, including branched or unbranched groups. The term "lower alkyl or alkenyl group" is intended to include saturated and unsaturated hydrocarbon groups with 1 to about 5 carbon atoms.

The embodiments where a and b are 0 and A is a carbonyl radical or a group having the structure:

wherein R$_4$ is a hydrogen atom or a lower alkyl or alkenyl group, have proven to be most useful embodiments to date.

Particularly preferred are compounds where a and b are 0, A is a carbonyl radical and R has the structure:

wherein R$_2$ and R$_3$ each is hydrogen atom, a methyl group or a ethyl group.

The compound also requires at least two nonpolar sections, designated B and B$_1$, which are attached to and connect polar groups. Additional nonpolar sections may also be present, e.g. B$_2$ when a is 1 and B$_3$ when b is 1. The nonpolar sections may comprise linear saturated hydrocarbon chains, linear unsaturated hydrocarbon chains containing one or more double or triple bonds, or saturated or unsaturated hydrocarbon chains containing one or more lower alkyl or alkenyl groups or small carbocyclic rings as substituents. In one of the preferred embodiments, the nonpolar groups are hydrocarbon chains comprising 4 to 7 methylene groups, especially preferred are hydrocarbon chains containing 6 carbon atoms.

Some of the preferred compounds for the practice of the present invention are those having the structures:

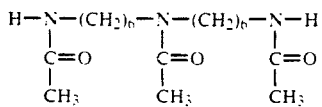

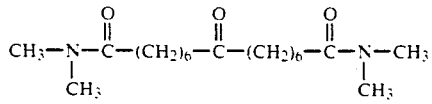

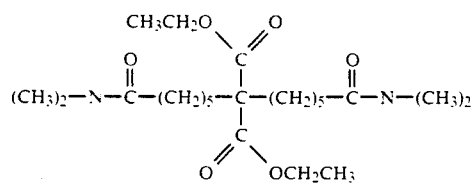

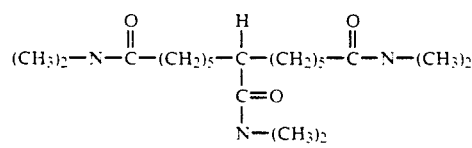

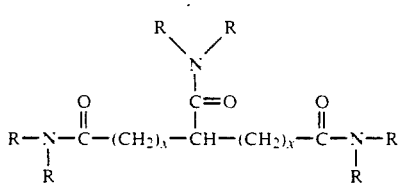

or

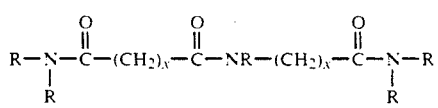

wherein R is hydrogen or a methyl group and x is 5 or 6.

Other compounds of this invention include a compound having the structure:

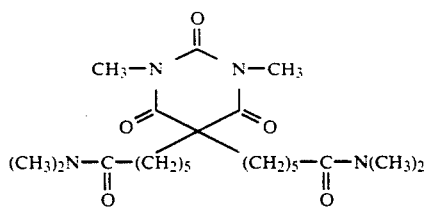

or a compound having the structure:

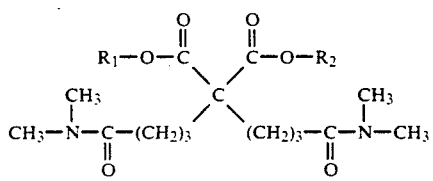

wherein R1 and R2 may be the same or different and each is a lower alkyl group.

Also provided by this invention is a compound having the structure:

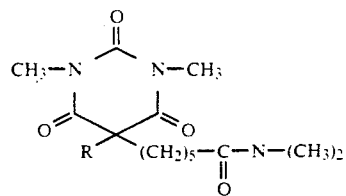

wherein R is H or a lower alkyl group.

This invention further provides a compound having the structure:

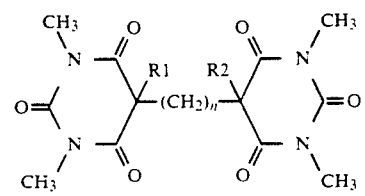

wherein n is an integer which is greater than 1 and R1 and R2 may be the same or different and each is H or a lower alkyl group.

A compound having the structure:

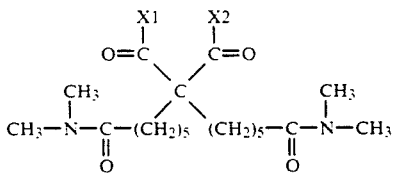

is also provided by this invention wherein X1 and X2 may independently be the same or different and each is $N(CH_3)_2$, NH-phenyl, or $HNCH_3$.

This invention also provides a compound having the structure:

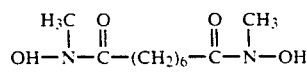

or a compound having the structure:

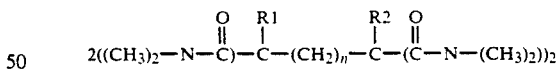

wherein R1 and R2 may be the same or different and each is H or a lower alkyl group;
and n is an integer from 1 to 10.

This invention further provides a compound having the structure:

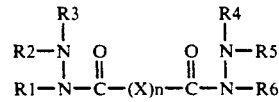

wherein R1, R2, R3, R4, R5, R6 may independently be the same or different from each other and is H or a lower alkyl group;
wherein X is methyl or phenyl; and
n is an integer from 1 to about 15.

A compound having the structure:

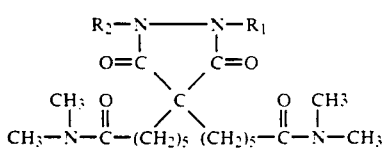

is also provided by this invention wherein R1 and R2 may be the same or different and is H or CH3.

The invention also provides a compound having the structure:

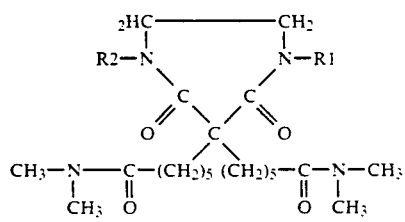

wherein $R_1$ and $R_2$ may be the same or different and is H or CH3.

A compound having the structure:

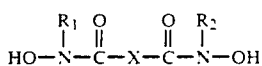

is provided by this invention, wherein X has the structure:

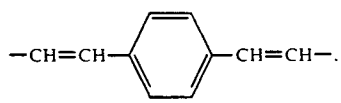

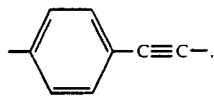

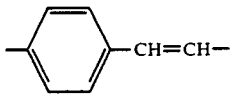

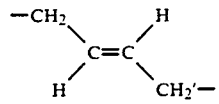

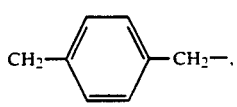

or

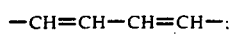

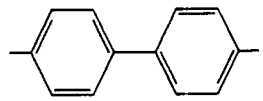

wherein $R_1$ and $R_2$ are the same or different and is H or lower alkyl group.

Further provided by this invention is a compound having the structure:

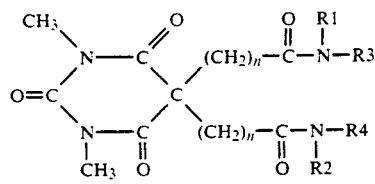

wherein R1 and R1 may independently be the same or different and each may be H or a lower alkyl group; wherein R3 and R4 may independently be the same or different and each may be CH3 or OH; and wherein n is 5 or 6.

A compound having the structure:

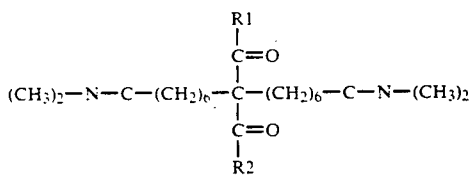

is also provided by this invention, wherein $R_1$ and $R_2$ is the same or different and is hydrogen, lower alkyl, alkenyl, alkynyl, an amide or hydroxyamide.

This invention further provides a compounds having the following structures:

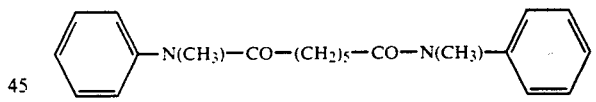

and

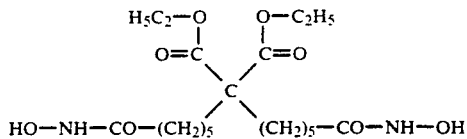

also,

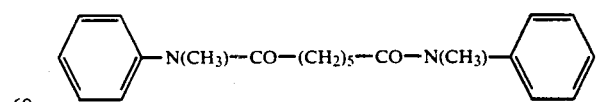

and a compound having the structure:

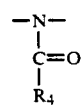

The invention also concerns a method of selectively inducing terminal differentiation of neoplastic cells and thereby inhibiting proliferation of such cells which comprises contacting the cells under suitable conditions with an amount of the compounds shown above effective to selectively induce terminal differentiation in the cells.

A method of selectively inducing terminal differentiation of neoplastic cells and thereby inhibiting proliferation of such cells is further provided by this invention which comprises contacting the cells under suitable conditions with an amount of a compound effective to selectively induce terminal differentiation, the compound having the structure:

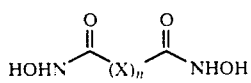

wherein X is phenyl or methyl and n is an integer from 1 to 15.

The contacting must be performed continuously for a prolonged period of time, i.e. for at least 48 hours, preferably for about 4-5 days or longer.

The method may be practiced in vivo or in vitro. If the method is practiced in vitro, contacting may be effected by incubating the cells with the compound. The concentration of the compound in contact with the cells should be from about 1 $\mu$M to about 25 mM, preferably from about 4 $\mu$M to about 5 mM.

However, for the compound having the structure:

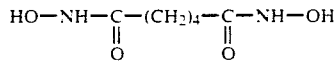

an amount of about 0.01 mM to about 10 mM has been shown to be effective.

The concentration depends upon the individual compound. For example, compound 12 of Table 1 should have a concentration from about 0.1 to about 2 mM, preferably from about 0.5 to about 0.7 mM. However, for the compounds listed in Table 4, the optimal concentration is as low as 5$\mu$M to about 5 mM. Another factor determining the preferable range is the state of the tumor cells. Thus, in cells which have low levels of vincristine resistance, the range of effective concentration of compound 12 from Table 1 is from about 0.01 to about 0.3 mM with a preferable range of about 0.05 to about 0.1 mM.

The invention also concerns a method of treating a patient having a tumor characterized by proliferation of neoplastic cells which comprises administering to the patient an amount of the compounds shown above, or with a compound having the structure:

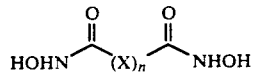

wherein X is phenyl or methyl and n is an integer from 1 to 15, effective to selectively induce terminal differentiation of such neoplastic cells thereby inhibiting their proliferation, and suppressing oncogenicity.

The method of the present invention is intended for the treatment of human patients with tumors. However, it is also likely that the method would be effective in the treatment of tumors in other animals. The term tumor is intended to include any cancer caused by the proliferation of neoplastic cells, such as lung cancer, acute lymphoid myeloma, bladder melanoma, renal carcinoma, breast carcinoma, or colorectal carcinoma. The administration of the compound to the patient may be effected orally or parenterally. To date, administration intravenously has proven to be effective. The administration of the compound must be performed continuously for a prolonged period of time, such as for at least 3 days preferably more than 5 days. In the most preferred embodiments, the administration is effected continuously for at least 10 days and is repeated at intervals wherein at each interval the administration is continuously effected for at least 10 days. For example, the administration may be effected at intervals as short as 5-10 days, up to about 25-35 days and continuously for at least 10 days during each such interval. The optimal interval period will vary depending on the type of patient and tumor. For example, in the incidence of acute leukemia, the so called myelodysplastic syndrome, continuous infusion would seem to be indicated so long as the patient tolerated the drug without toxicity and there was a positive response.

The amount of the compound administered to the patient is less than an amount which would cause toxicity in the patient. In the certain embodiments, wherein the compounds have the structures:

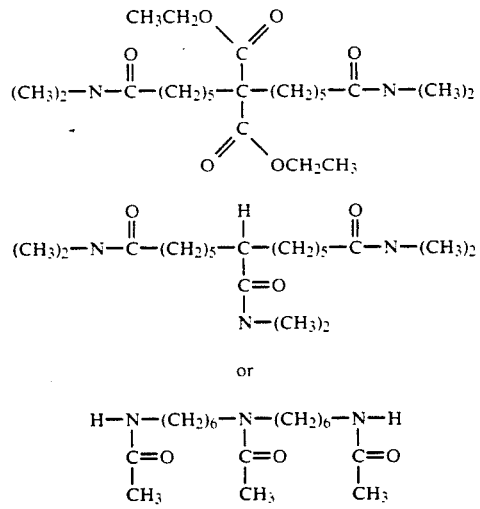

the amount of the compound which is administered to the patient is less than the amount which causes a concentration of the compound in the patient's plasma to equal or exceed the toxic level of the compound. Preferably, the concentration of the compound in the patient's plasma is maintained at about 1.0 mM. It has been found with HMBA, that administration of the compound in an amount from about 5 gm/m$^2$/day to about 30 gm/m$^2$/day, particularly about 20 gm/m$^2$/day, is effective without producing toxicity in the patient. For the compound shown above, in vitro studies have shown that the optimal amount of the compounds is substantially lower than 30 gm/m$^2$/day, and may even be lower than 1 gm/m$^2$/day. The optimal amount of the compound which should be administered to the patient in the practice of the present invention will depend on the particular compound used and the type of cancer being treated.

This invention, in addition to the above listed compounds, is intended to encompass the use of homologs and analogs of such compounds. In this context, homologs are molecules having substantial structural similarities to the above-described compounds and analogs are molecules having substantial biological similarities regardless of structural similarities.

The invention also concerns a pharmaceutical composition comprising a pharmaceutically acceptable carrier, such as sterile pyrogen-free water, and any of the compounds listed above in an amount less than an amount which if administered intravenously or orally to a patient would cause the patient's blood plasma concentration of the compound to exceed toxic levels.

The invention is illustrated in the Experimental Detail section which follows. This section is set forth to aid in an understanding of the invention but is not intended to, and should not be construed to, limit in any way the invention as set forth in the claims which follow thereafter.

EXPERIMENTAL DETAILS

Methods

Cells and Materials

MELC 745A-DS19 cells and the variants of MELC derived from this cell line, namely, the vincristine-resistant MELC V3.17 and VCR.C(2)15 cell lines (26), and the dimethylsulfoxide-resistant cell line, DR10 (37), were maintained in alpha minimal essential medium containing 10% fetal calf serum (16). Cell cultures for all experiments were initiated with : cells in logarithmic growth phase (day 2 cultured cells) at a density of $10^5$ cells/ml Inducer compounds were added in the final concentrations indicated below, dissolved in culture medium without fetal calf serum unless otherwise indicated. Cell density and benzidine reactively were determined as described (16).

Commitment to terminal differentiation, characterized by limited cell division (colony size < 32 cells) and accumulation of hemoglobin (benzidine reactive colonies) was assayed by a colony cloning assay using 2% methylcellulose as described (25).

TABLE 1

| CPD # | Structure | Mol Wt. | Optimal Concentration (mM) | Benzidine Reactive Cells (%) | Commitment (%) |
|---|---|---|---|---|---|
| 1. | $CH_3-CO-NH-(CH_2)_6-NH-CO-CH_3$ | 200 | 5 | >95 | >95 |
| 2. | $CH_3-NH-CO-CH_3$ | 75 | 50 | −70 | NO |
| 3. | $CH_3-CO-NH-(CH_2)_2-CH(CH_3)-(CH_2)_2-NH-CO-CH_3$ | 200 | 5 | >95 | >95 |
| 4. | $CH_3-CO-NH-(CH_2)_3-CH(CH_3)-CH_2-NH-CO-CH_3$ | 200 | 5 | >95 | >90 |
| 5. | $CH_3-CO-NH-CH_2-CH(CH_3)-CH(CH_3)-CH_2-NH-CO-CH_3$ | 200 | 5 | >95 | NO |
| 6. | $CH_3CH_2-CO-NH-(CH_2)_5-NH-CO-CH_2CH_3$ | 218 | 5 | >90 | >90 |
| 7. | $CH_3-NH-CO-(CH_2)_6-CO-NH-CH_3$ | 200 | 5 | >95 | >90 |
| 8. | $(CH_3)-N-CO-(CH_2)_6-CO-N-(CH_3)_2$ | 228 | 5 | >90 | >90 |
| 9. | $(CH_3)_2-N-CO-(CH_2)_7-CO-N-(CH_3)_2$ | 242 | 2 | >90 | >90 |
| 10. | $HN-(CH_2)_6-N-(CH_2)_6-NH$ with three $C(=O)-CH_3$ groups | 341 | 2 | >90 | >90 |

TABLE 1-continued

| CPD # | Structure | Mol Wt. | Optimal Concentration (mM) | Benzidine Reactive Cells (%) | Commitment (%) |
|---|---|---|---|---|---|
| 11. | $(CH_3)_2-N-\overset{O}{\overset{\|}{C}}-(CH_2)_5-\overset{H}{\underset{\underset{\underset{N-(CH_3)_2}{\|}}{\underset{C=O}{\|}}}{C}}-(CH_2)_5-\overset{O}{\overset{\|}{C}}-N-(CH_3)_2$ | 369 | 2.5 | >90 | >90 |
| 12. | $(CH_3)_2-N-\overset{O}{\overset{\|}{C}}-(CH_2)_5-\underset{\underset{OCH_2CH_3}{\overset{\|}{\underset{O}{C}}\diagdown}}{\overset{\overset{CH_3CH_2O\diagdown\overset{O}{\diagup}C\diagup}{\|}}{C}}-(CH_2)_5-\overset{O}{\overset{\|}{C}}-N-(CH_3)_2$ | 442 | 0.6 | >90 | >90 |

TABLE 2

|  |  |  | 24 h | | 48 h | | 120 h | | commitment | |
|---|---|---|---|---|---|---|---|---|---|---|
|  |  |  | cell count | B− | cell count | B− | cell count | B− | 24 h | 48 h |
| HMBA | 1 mM | DS19 | 0.4 | 0-1 | 1.0 | 0-1 | 3.0 × 10⁶ | 8% | 0-1 | 6-8 |
|  |  | V₃17 | 0.38 | 8-9 | 0.8 | 33% | 2.8 | 58% | 30% | 43% |
|  | 2 mM | DS19 | 0.42 | 0-1 | 0.9 | 0-1 | 2.9 | 64% | 0-1 | 71% |
|  |  | V₃17 | 0.4 | 7-9 | 0.8 | 72% | 2.6 | 89% | 39% | 79% |
|  | 3 mM | DS19 | 0.4 | 0-1 | 0.9 | 2% | 2.8 | 82% | 0-1 | 81% |
|  |  | V₃17 | 0.3 | 9-10 | 0.8 | 80% | 1.8 | 91% | 77% | 94% |
|  | 4 mM | DS19 | 0.3 | 0-1 | 0.8 | 11% | 2.6 | 94% | 4% | 92% |
|  |  | V₃17 | 0.28 | 9-13 | 0.4 | 88% | 1.6 | 96% | 80% | 99% |
|  | 5 mM | DS19 | 0.23 | 0-1 | 0.5 | 14% | 2.4 | 98% | 6% | 96% |
|  |  | V₃17 | 0.22 | 9-14 | 0.5 | 89% | 1.6 | 99% | 83% | 98% |
| IC-135 | 1 mM | DS19 | 0.3 | 0-1 | 0.6 | 0-1 | 1.6 | 69% | 0-1 | 71% |
|  |  | V₃17 | 0.3 | 8-9 | 0.6 | 83% | 1.3 | 89% | 58% | 89% |
|  | 2 mM | DS19 | 0.3 | 0-1 | 0.5 | 0-1 | 1.3 | 79% | 1-2 | 87% |
|  |  | V₃17 | 0.29 | 7-6 | 0.4 | 88% | 1.3 | 94% | 70% | 95% |
|  | 3 mM | DS19 | 0.27 | 0-1 | 0.4 | 0-1 | 1.3 | 86% | 5-4 | 91% |
|  |  | V₃17 | 0.12 | 8-6 | 0.3 | 89% | 0.9 | 96% | 76% | 97% |
|  | 4 mM | DS19 | 0.13 | 0-1 | 0.2 | 0-1 | 0.6 | 78% | 2-1 | 79% |
|  |  | V₃17 | 0.18 | 6-8 | 0.19 | 34% | 0.5 | 79% | 44% | 81% |
|  | 5 mM | DS19 | 0.12 | 0 | 0.13 | 0-1 | 0.4 | — | 8% | — |
|  |  | V₃17 | 0.12 | 8-11 | 0.12 | 0-1 | 0.3 | — | 0-1 | — |
| CONTROL |  |  | 0.4 | 5-9 | 1.0 | 0.1 | 3.1 × 10⁶ | 0-1 | 0-1 | 0-1 |

IC-135 50 mM Stock.
40 λ - 1 mM
200 λ - 5 mM
HMBA 200 mM Stock
10 λ - 1 mM
50 λ - 5 mM

TABLE 3

TESTING OF IC-135 ON DIFFERENT MELC LINES

| DS-1 g | 1st Day | 2nd Day | 5th Day Cell Count | 5th B⁺ | (5 day commitment) |
|---|---|---|---|---|---|
| Control | 0.38 | 1.1 | 2.8 | 0-1 | 0-1 |
| 5 mM HMBA | 0.2 | 0.5 | 2.0 | 91-90 | 88-88 |
| 0.5 mM IC-135 | 0.38 | 1 | 2.1 | 41-49 | 31-28 |
| 1 mM IC-135 | 0.33 | 0.8 | 1.4 | 72-74 | 51-58 |
| 2 mM IC-135 | 0.2 | 0.5 | 1.3 | 80-80 | 78-76 |
| 3 mM IC-135 | 0.2 | 0.5 | 1.2 | 87-88 | 81-80 |

| V3-17 | 1st Day | 2nd Day | 5th Day | 5th B⁺ | (5 day commitment) |
|---|---|---|---|---|---|
| Control | 0.4 | 1.2 | 2.9 | 3-6 | 0-1 |
| 5 mM HMBA | 0.23 | 0.5 | 1.6 | 98-99 | 99-98 |
| 0.5 mM IC-135 | 0.4 | 0.6 | 2.7 | 40-49 | 36-34 |
| 1 mM IC-135 | 0.31 | 0.44 | 1.3 | 89-83 | 89-91 |
| 2 mM IC-135 | 0.21 | 0.4 | 1.0 | 96-91 | 92-94 |
| 3 mM IC-135 | 0.23 | 0.3 | 0.9 | 98-97 | 99-99 |

| DR-10 | 1st Day | 2nd Day | 5th Day | 5th B⁻ | 5th day commitment |
|---|---|---|---|---|---|
| Control | 0.41 | 1.0 | 2.9 | 0-1 | 0-0 |
| 5 mM HMBA | 0.3 | 0.48 | 2.1 | 90-89 | 1-4 |
| 0.5 mM IC-135 | 0.4 | 0.62 | 1.9 | 44-39 | 0-0 |
| 1 mM IC-135 | 0.32 | 0.48 | 1.4 | 70-74 | 0-1 |
| 2 mM IC-135 | 0.2 | 0.41 | 1.2 | 79-81 | 0-2 |
| 3 mM IC-135 | 0.2 | 0.40 | 1.2 | 88-86 | 1-3 |

CHEMISTRY

HMBA, compound 1 of Table 1, (9) was obtained from Aldrich Chemical Co.

The preparation and characterization of compounds 1, 2, 6, 7, 8 and 9 of Table 1 (9,27) was previously described. All new amides were purified by chromatography on alumina with 5% methanol in methylene chloride, and were judged pure by thin layer chromatography (single spot) and ¹H NMR spectroscopy. Final products were characterized by ¹H NMR, infrared, and CI mass spectroscopy, while intermediates were characterized by $^1$H NMR spectra. The data were consistent with the assigned structures (expected infrared and NMR signals, M+1 mass spectra).

For the synthesis of compound 3 (Table 1), the known 3-methyl-1,5-dibromopentane (38) was converted to the bis-phthalimide derivative, and this was cleaved with hydrazine to afford 3-methyl-1,5-diaminopentane, isolated as the dihydrochloride (m.p. 123-126°). This was converted to compound 3 with acetic anhydride and triethylamine in dioxane.

Compound 4 (Table 1) (m.p. 67-68°) was obtained in quantitative yield by similar acetylation of commerically available 2-methyl-1,5-diaminopentane.

Compound (Table 1) was synthesized from meso-2,3-dimethylsuccinic acid in six steps. Reduction of the dimethyl ester with LiAlH$_4$ afforded the meso-2,3-dimethylbutanediol (92% yield). This was converted to the bis-tosylate, and then to the bis-phtalimide. Deprotection and acetylation as before gave compound 5 as an oil (61% yield from the diol).

Compound 10 (Table 1) was prepared by making a solution of 1,4-dioxane at room temperature under argon. Then 44.8 ml. of triethylamine was added, and 20.3 ml. of acetyl chloride was slowly added with stirring. After two hours of stirring at room temperature the triethylamine hydrochloride was removed by filtration and the filtrate was concentrated in vacuo. The product triacetyl compound was isolated as a clear viscous oil at about 90% yield by chromatography on basic alumina using isopropanol/ethyl acetate/dichloromethane in the ratio 2/3/5. On thin layer plates of basic alumina with this solvent mixture the product had an R$_f$ of ca. 0.6.

The mass spectrum (chemical ionization, NH$_3$ carrier) showed peaks at 342 (100%, M+1), 227 (10%) and 115 (22%). The infrared spectrum (thin film on NaCl) had bands at 3288, 2931, 2858, 1627, 1560, 1437, 1373, and 1292 cm$^{-1}$. In the proton NMR (CDCl$_3$) the acetyl groups appeared at 6.10 as a broad signal, while the methylene protons appeared as multiples with the expected intensities in the regions of 3.12 to 3.30 and 1.21 to 1.54.

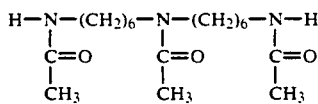

For preparation of the triamide compound 11 (Table 1), dimethyl malonate was dialkylated with ethyl 6-bromohexanoate under standard conditions. The resulting tetraester was then hydrolyzed and thermally monodecarboxylated to 1,7,13-tridecanetricarboxylic acid. Treatment with thionyl chloride followed by diethylamine afforded compound 11 (Table 1).

Compound 12 (Table 1) was prepared by simple dialkylation of dimethyl malonate with the know N,N'-dimethyl-6-bromohexanecarboxamide (39).

The compound having the structure:

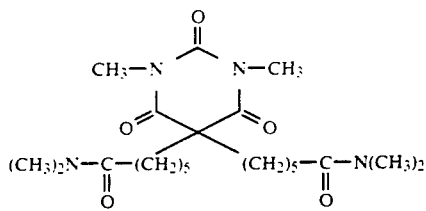

was made as follows. 1,3-dimethylbarbituric acid (5g; 0.032 mol) in DMF (100 ml) was slowly added to a suspension of sodium hydride (1.5g; 0.064 mol) in DMF (300 ml). The suspension was stirred at 80° C. for five hours. N,N-Dimethyl 6-bromohexanoylamide (14.3 g; 0.064 mol) in DMF (100 ml) was added to the cool suspension with stirring. The resulting suspension was stirred at 120° C. overnight. The DMF was evaporated and the residue was partitioned between chloroform and water (100-100 ml). The chloroform layer was separated, and the water layer was extracted with chloroform (5×50 ml). The combined chloroform layers were dried over anhydrous magnesium sulfate, and evaporated. The oily in ethyl acetate-tetrahydrofuran (2:1). The yield of 1,3-dimethyl-5,5-di (N,N-dimethyl-5-pentylcaboxamide)barbituric acid was 4.1 g (30%).

$^1$H NMR (CDCl$_3$, 200 MHz) δ3.33(s, bar, N-CH3,6H), 2.98 (s, N-CH3, 6H), 2.93 (s, N—CH3, 6H), 2.24 (t, J=7 Hz, CH2CON, 4H), 1.96 (m, 4H), 1.58 (m, 4H), 1.28 (m, 4H), 1.08 (m, 4H). The compound having the structure:

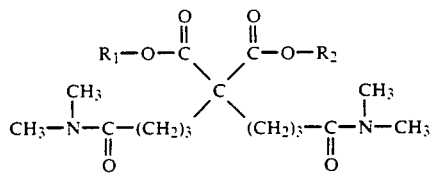

was made as follows. Diethyl malonate (50.6 ml; 53.3 g; 0.33 mol) in DMF (150 ml) was added slowly to a cool suspension of sodium hydride (16 g; 0.67 mol) in DMF (1 liter). The suspension was carefully heated with stirring at 80° C. (about one hour). The clear mixture was cooled, and N,N-dimethyl 6-bromohexanoylamide (146.5 g; 0.66 mol) in DMF (200 ml) was slowly added at room temperature. The suspension was stirred at 110° C. for two hours, and the DMF was evaporated. The semisolid residue was partitioned between chloroform and water (about 200-200 ml). The organic layer was separated, and the water layer was extracted with chloroform (5×100 ml). The combined chloroform layers were dried over anhydrous magnesium sulfated and evaporated. The oily residue was purified by column chromatography on silica gel in ethyl acetate-tetrahydrofuran (4:1). The yield of diethyl undecane-6,6-di(ethylcarboxylate)-1,11-di(N,N-dimethlycarboxamide) was 106 g (76%).

$^1$H—NMR(CDCl3, 200 MHz) δ4.11(q, J=7.0 Hz, 4H), 2.96 (t,J=7.5Hz, 1H), 2.89(s,6H), 2.25(t, J=7.2Hz, 4H), 1.88 (m, 4H), 1.59 (m, 4H), 1.16-1.31 (m,14H).

IR (NaCl, CH2Cl2) 2937, 2866, 1728, 1642, 1498, 1462, 1399, 1369, 1265, 1153, 1097, 1029 cm$^{-1}$.

MS glycerol) m/e=443 (40%, M+1$^+$), 398 (25%), 295 (80%), l42 (45%).

The compound having the structure:

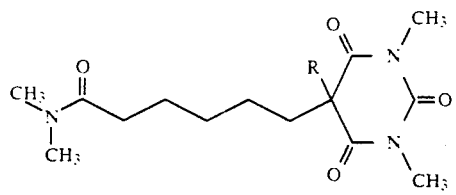

was made as follows. 1,3,5,-trimethylbarbituric acid (1.7 g; 10 mmol) in DMF (20 ml) was added at room temperature to a suspension of sodium hydride (0.24 g; 10 mmol) in DMF (100 ml). The suspension was stirred at 90.C for one hour. N,N-Dimethyl 6-bromohexanoylamide (2.22 g; 10 mmol) in DMF (20 ml) was added to a cool mixture (about 5° C.). The suspension was stirred at 110° C. overnight. DMF was evaporated, and the residue was partitioned between chloroform and water (50-50 ml). The chloroform layer was separated, and the water layer was extracted with chloroform. The combined chloroform layers were dried over anhydrous magnesium sulfate and evaporated. The oily residue was purified by column chromatography on silica gel in ethyl acetate-tetrahydrofuran. The yield of 1,3-dimethyl-5-methyl-5-(5-pentyl-N,N-dimethylcarboxamide)barbituric acid was 1.5 g(48%).

$^1$H NMR (CDCl$_3$, 200 MHz) δ3.23(s, bar.H, N—CH3,6H), 2.99 (s, N—CH3, 3H), 2.94 (s, N—CH3, 3H), 2.26 (t, J=7.2 Hz, CH2CON, 2H), 1.98 (m, 2H), 1.62 (m, 2H), 1.52 (m, C-Me, 3H), 1.32 (m, 2H), 1.11 (m, 2H).

The compounds having the structure:

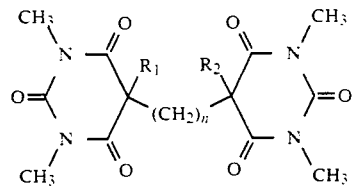

were made as follows. 1,3,5-trimethylbarbituric acid (0.71 g; 0.029 mol)in DMF (10 ml) was added to a suspension of sodium hydride (0.71 g; 0.029 mol) in DMF (20 ml). The suspension was stirred at 80° C. for one hour. 1,n-dibromoalkane (0.0147 mol) was added to a cool suspension (about 5° C.). The reaction mixture was heated at 110° C. for four hours, cooled down and evaporated. The solid residue was slurried in water (about 200 ml), filtered, and the white solid was washed with water (3×5 ml), ethanol (3×20 ml), and ether (2×20 ml). The yield of dibarbiruric acids were for: n=3, 75%; n=4, 78%; n=5, 71%; n=6, 79%; n=7, 83%.

$^1$H NMR for the compound With n=2 (CDCl$_3$, 200 MHz) δ3.32(s, N—CH3, 12H), 1.86 (s,CH2,4H), 1.47 (s, C—CH3,6H).

The compounds having the structure:

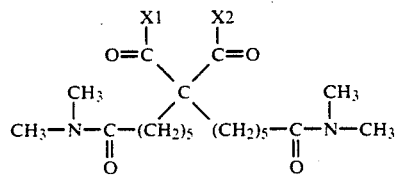

were made as follows. When X1 and X2 are the same and each is HNCH3, aqueous (10 ml) potassium hydroxide (1.53 g; 27.5 mmol) was added to the diamidebarbituric acid (2.4 g; 5.5 mmol) in water (50 ml). The mixture was stirred at 70° C. for fifteen minutes, cooled, filtered, acidified, and extracted by chloroform (5×20 ml). The combined chloroform extracts were dried over anhydrous magnesium sulfate and evaporated to the oily residue. By the NMR, hexamethylamide was more than 96% pure. The yield of undecane-1,11-di-(N,N-dimethylcarboxamide)-6,6-di(N-methylcarboxamide) was 2.1 g (93%).

$^1$H NMR (CDCl$_3$, 200 MHz) δ7.38 (q, J=8 Hz), 3.03 (s, N—CH3,6H), 2.94 (s,N—CH3,6H), 2.8 (d, J=8 Hz, N—CH3,6H), 2.32 (t, J=7.2 Hz, CH2CON, 4H), 2.82 (m, 4H), 2.62 (m, 4H), 1.25 (m, 8H).

When X1 and X2 are the same and each is N(CH3)2, the hexamethylamide (2 g; 4.9 mol) in DMF (10 ml) was added at room temperature to a suspension of sodium hydride (0.24 g; 0.01 mol) in DMF (20 ml). The mixture was stirred at 80° C. for one hour. Methyl iodide (3.5 ml; 8 g; 56 mmol) was added with stirring to the cool reaction mixture. The reaction was continued at 60° C. overnight. The solvent was evaporated and the solid residue was dissolved in water (50 ml) and the water solution was extracted with 8:2 chloroform-methanol (5×50 ml). The combined organic layers were dissolved in acetone (200 ml) and filtered through a short column of silica gel. Acetone was evaporated yielding pure undecane-1,6,6,11-tetra-(N,N-dimethylcarboxamide) (1.36 g; 63%).

$^1$H NMR (CDCl$_3$) δ2.99 (s, N—CH3, 6H), 2.94 (s, N—CH3, 6H), 2.92 (s, N—CH3, 6H), 2.88 (s, N—CH3, 6H), 2.28 (t, J=7.2 Hz, CH2CON, 4H), 1.86 (m, 4H), 1.62 (m, 4H), 1.32 (m, 8H).

The compounds having the structure:

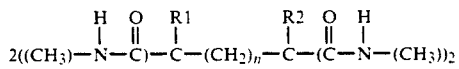

wherein n is an integer from 1 to 15 are made as follows. A dibarbituric acid (3.66 g; 0.01 mol for n 2) was suspended in 9:1 water-dioxane (60 ml) and heated up to 100° C. To this suspension was added at 110° C. a solution of potassium hydroxide (5.6 g; 0.1 mol/20 ml water for n=2). The suspension immediately became a solution. The solution was heated at 110° C. for an extra 10 minutes, cooled down, filtered, and acidified. The clear water solution was extracted with chloroform (10×50 ml). The combined chloroform extracts were dried over anhydrous magnesium sulfate, and evaporated. The yields of the alkane-l,l,n,n,-tetra-(N-methylcarboxamide) were for: n=2, 85%; n=3, 79%; n=4, 83%; n=5, 81%; n=6, 74%; n=7, 83%.

$^1$H NMR (CDCl$_3$, 200 MHz) for compounds having n=2, δ7.92 (q, J=4.6 Hz, NH-Me, 4H), 2.85 (d, J=4.6 Hz, N—CH3, 12H), 1.85 (s, CH2, 4H), 1.43 (s, C-CH3, 6H).

The compounds having the structure:

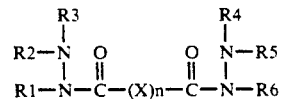

wherein R1, R2, R3, R4, R5, R6 may independently be the same or different from each other and is H or a lower alkyl group; wherein X is methyl or phenyl; and n is an integer from 1 to about 15, were made as follows. When R1 and R6 is each H and R2, R3, R4, and R5 is each CH3, to a chloroform (200 ml) solution of suberoyl chloride (8 g; 38 mmOl) was added at room temperature to 1,1-dimethylhydrazine (11.5 ml; 9.1 g; 152 mmol). The mixture was stirred at room temperature for about three hours. The solvent was evaporated, and the residue was dissolved in methanol (400 ml). The methanol was evaporated and the solid residue was dissolved in water (100 ml). The water solution was extracted with hexanes (5×50 ml), and with chloroform (5 ×50 ml). The combined extracts were dried over anhydrous magnesium sulfate and evaporated. The solid residue was crystallized from acetone. The yield of hexane-1,6-di($N^2,N^2$-dimethyl-carboxhydrazide) was 6.5 g (66%).

When R1, R2, R3, R4, R5, and R6 is each CH3, to a suspension of sodium hydride (1.4 g; 57.9 mmol) in DMF (60 ml) at room temperature was added tetramethylhydrazide (5 g; 19.3 mmol) followed by methyl iodide (31.5 ml; 71.8 g; 579 mmol). The reaction mixture was stirred at 60° C. for five hours. The DMF was evaporated, and the solid residue was dissolved in water (50 ml) and extracted with chloroform (5×50 ml). The chloroform extracts were dried over anhydrous magnesium sulfate and evaporated. The product was purified by crystallization from hexanes. The yield of hexane-1,6-di($N^1$, $N^2$, 2-trimethylcarboxhydrazide) was 3.7 g (67 %).

The compounds having the structure:

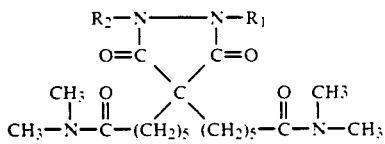

may be made as follows. The heterocyclic compounds may be alkylated after they are formed from malonic chloride and $N,N^1$-dialkylahydrazine.

The compounds having the structure:

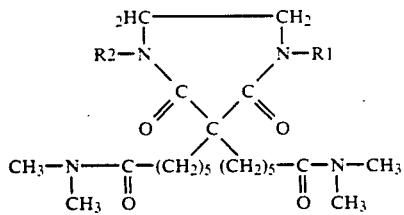

wherein $R_1$ and $R_2$ may be the same or different and is H or CH3 may be made as follows. The heterocyclic part of the compound may be made from malonic chloride and $N,N^1$-dealkylethylenediamine. The heterocyclic compound may then be alkylated with the corresponding alkyl bromide under known conditions.

The compounds having the structure:

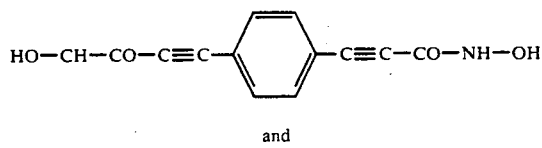

and

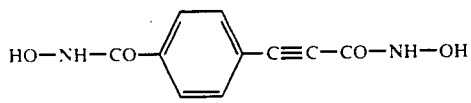

may be synthesized from the corresponding acid via acidic chloride with hydroxylamine hydrochloride in a solution of tetrahydrofuran and water. The acid may be made from 1,4-benzenediacrylic acid by an addition of bromine, and following elimination with base.

The compound having the structure:

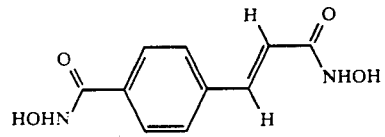

was made as follows. A suspension of 4-carboxycinnamic acid (10 g; 0.052 mol) and thionyl chloride (15.2 ml), 24.8 g; 0.208 mol) in benzene (500 ml) was refluxed for five hours. The solvent was evaporated and the oily residue was dissolved in tetrahydrofuran (100 ml). The tetrahydrofuran solution was slowly added at about 5° C. to a stirred water solution (100 ml) of hydroxylamine hydrochloride (7.3 g; 0.104 mol) and potassium hydroxide (11.6 g; 0.208 mol). A white precipitate was formed immediately. The suspension was stirred at room temperature for two hours, and filtered. The solid was washed with cooled water (5×20 ml) and acetone (5×20 ml). The solid was slurried in methanol (3 liters), and the suspension was refluxed. The hot suspension was filtered. The filtrate was concentrated to 100 ml and cooled. The white crystals were separated by filtration, and washed with acetone (3 x 20 ml) and ether (5 ×20 ml). The yield of benzene-1-(N-hydroxycarboxamide)-4-[trans-ethene-2-(N-hydroxycarboxamide)] was 5.2 g (45%).

$^1$H NMR (DMSO-$d_6$, 200 MHz), 11.05 (broad s, OH, 2H), 9.12 (broad s, NH, 2H), 7.77 (d, J=8.2 Hz, arom. H, 2H), 7.62 (d, J=8.2 Hz, arom. H, 2H), 7.47 (d, J=15.8 Hz, CH, 2H), 6.53 (d, J=15.8 Hz, CH, 2H).

The compound having the structure:

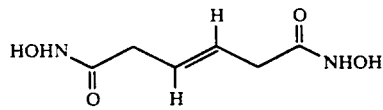

was made as follows. A suspension of trans-B-hydromuconic acid (5 g; 0.0347 mol), oxalyl chloride (12 ml; 17.6 g; 0.139 mol) in benzene (250 ml) and a few drops of DMF was stirred at room temperature until the reaction suspension became clear (about one hour). The solvent was evaporated, and the oily residue was dissolved in tetrahydrofuran (50 ml). The tetrahydrofuran solution was slowly added into cool (about 5° C.) aqueous solution of hydroxylamine hydrochloride (4.8 g; 0.0694 mol) and potassium hydroxide (7.8 g; 0.1388 mol). The reaction suspension was stirred at room temperature for about one hour and evaporated to a volume of 20 ml. The suspension was cooled and filtered. The crude solid product was slurried in methanol (200 ml) and the suspension was cooled and filtered. The filtrate was dried over anhydrous magnesium sulfate, and evaporated ml)

and recovered by filtration. The yield of trans-2-butene-1,4-di-(N-hydroxylcarboxamide) was 3.8 g (63%).

¹H NMR (DMSO-d₆, 200 MHz), δ10.85 (s, OH, 2H), 9.08 (s, NH, 2H), 7.11 (d of d, J¹=11.2 Hz, J²=2.8 Hz, CH, 2H), 6.17 (d of d, J¹=11.4 Hz, J²=2.8 Hz).

The compound having the structure:

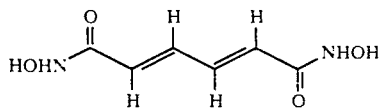

was made as follows. A solution of trans, trans-muconic acid (5 g; 0.035 mol), oxalyl chloride (12.3 ml, 17.9 g; 0.141 mol) and a few drops N,N-dimethyl formamide in benzene (250 ml) was stirred at room temperature for three hours. The solvent was removed under reduced pressure. The oily residue was dissolved in tetrahydrofuran (50 ml) and the tetrahydrofuran solution was added dropwise to the stirred solution of hydroxylamine hydrochloride (4.9 g; 0.074 mol) and potassium hydroxide (7.9 g; 0.141 mol) at about 5° C. A white precipitate was formed immediately. The suspension was stirred at room temperature for about one hour and filtered. The solid was slurried in methanol (2 liters) and the suspension then was boiled and filtered. The methanol solution was concentrated to a volume of about 20 ml. The solid product was separated by filtration and washed with ether (5×20 ml). The yield of trans,trans-1,3-butadiene-1,4-(N-hydroxylcarboxamide) was 3.1 g (52%).

¹H NMR (DMSO-d₆, 200 MHz), 10.46 (s, 2H, OH), 8.75 (s, 2H, NH), 5.53 (t, J=3.4 Hz, CH, 2H), 2.70 (d, J=3.4 Hz, 4H, CH2).

The compound having the structure:

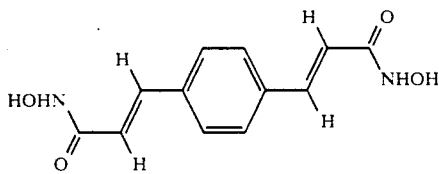

was made as follows. A suspension of 1,4-phenylenediacrylic acid (10 g; 0.184 mol) and thionyl chloride (13.4 ml; 21.9 g; 0.184 mol) in benzene (500 ml) was refluxed for five hours. The clear solution was cooled, and the solvent was evaporated. The oily residue was dissolved in tetrahydrofuran (100 ml) and slowly added into cooled (about 5° C.) aqueous (100 ml) solution of hydroxylamine hydrochloride (6.4 g; 0.092 mol) and potassium hydroxide (10.3 g; 0.184 mol). A white precipitate was formed immediately. The suspension was stirred at room temperature (two hours), and filtered. The crude product was slurried in boiling water (100 ml), and the suspension was filtered. The solid was slurried in acetone (200 ml) and boiled. The hot suspension was filtered, and the solid was washed with acetone (5×20 ml), and then with ether (5×20 ml). The yield of benzene-1,4-di[trans-ethene-2-(N-hydroxulcarboxamide)] was 6.2 g (54%).

¹H NMR (DMSO-d₆, 200 Hz), δ10.82 (s, OH, 2H), 9.17 (s, NH, 2H), 7.58 (s, C₆H₄, 4H), 7.45 (d, J=15.8 Hz, CH, 4H), 6.51 (d, J=15.8 Hz).

The compound having the structure:

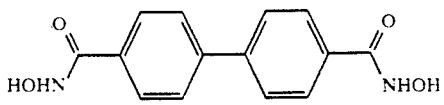

was made as follows. A suspension of 4,4-diphenyldicarboxylic acid (5 g; 20.6 mmol) and thionyl chloride (7.3 ml; 12 g; 0.1 mmol) in benzene (250 ml) was refluxed overnight. The clear solution was cooled, and the solvent was evaporated. The solid residue was dissolved in tetrahydrofuran (100 ml) and was added slowly into a cool (about 5° C.) aqueous (100 ml) solution of hydroxylamine hydrochloride (2.9 g; 41.7 mmol) and potassium hydroxide (4.65 g; 83 mmol). A white precipitate was formed immediately. The suspension was stirred at room temperature for about two hours and filtered. The crude product was slurried in water (50 ml) and the resulting suspension was boiled (about 10 minutes). The solid was separated by filtration, and slurried in acetone (200 ml) and boiled. The hot suspension was filtered, and the solid was washed with acetone (5×50 ml), and then with ether (5×20 ml). The yield of diphenyl-4,4'-di-(N-hydroxylcarbox-amide) was 4.9 g (88%).

¹H NMR (DMSO-d₆, 200 MHz), δ11.33 (s, OH, 2H), 9.12 (broad s, NH, 2H), 7.87 (d, J=8.2 Hz, arom. H, 2H), 7.80 (d, J=8.4 Hz, arom. H, 2H).

The compound having the structure:

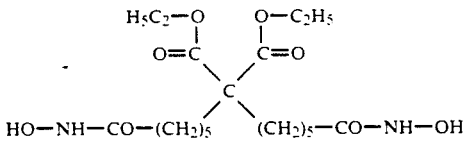

was made as follows. Diethyl malonate (15.2 ml; 16 g; 0.1 mol) was slowly added at room temperature to a suspension of sodium hydride (4.8 g; 0.2 mol) in N,N-dimethyl formamide (300 ml). The suspension was heated at 80° C. for about one hour and cooled down. Benzyl-6-bromohexanoate (57 g; 0.2 mol) was added at room temperature with vigorous stirring. The suspension was heated at 100° C. for about 5 hours and the DMF was evaporated. The residue was partitioned between chloroform and water (200-200 ml). The chloroform layer was separated and the water layer was extracted with chloroform (5×50 ml). The combined chloroform layers were dried over anhydrous magnesium sulfate, and evaporated. The oily residue was purified by column chromatography on silica gel in hexanes-ethyl acetate. The yield of undecane-6,6-di(ethylcarboxylate)-1,11-di(benzylcarboxylate) was 41 g (72 %). Dibenzyl 6,6-di(ethoxycarbonyl)-1,11-undecanedicarboxylate (20 g; 35.2 mmol) was dissolved in methanol (150 ml) and 5% Pd-C (200 mg) was added. The reaction suspension was hydrogenated at room temperature overnight. The catalyst was removed by filtration, and the methanol was evaporated yielding pure 6,6-(ethylcarboxylate)-1,11-undecanedicarboxylic acid (12.5 g; 93%).

The acid was suspended in benzene (500 ml), and oxalyl chloride (11.2 ml; 16.3 g; 0.129 mol) and a few drops of DMF were added. The mixture was stirred at room temperature for about 3 hours. The solvent was evaporated and the oily residue was dissolved in chloroform (100 ml). The chloroform solution of the acid chloride was slowly added to a stirred solution of 0-benzylhydroxylamine (16.3 g; 0.132 mol) in chloroform (300 ml). A white precipitate was formed immediately. The suspension was filtered, and concentrated hydrochloric acid was added (50 ml) to the chloroform filtrate and again filtered. The chloroform layer was washed with concentrated hydrochloric acid (3×100 ml), water (3×100 ml), and dried over anhydrous magnesium sulfate. The chloroform was evaporated yielding pure N,N'-dibenzyloxy-6,6-di(ethoxycarbonyl)-1,11-undecanedicarboxamide (17.1 g; 89%).

The benzyloxyamide (6 g; 0.01 mol) was dissolved in methanol (50 ml), and 5% Pd-C (200 mg) was added. The methanol suspension was hydrogenated at room temperature overnight. The catalyst was separated by filtration and methanol was evaporated yielding pure undecane-6,6-di(ethylcarboxylate)-1,11-di(N-hydroxylcarboxamide) (3.9 g; 93%). The overall yield was 55.4%.

$^1$H NMR (DMSO-d$_6$, 200 MHz), 10.30 (broad s, OH, 2H), 8.75 (broad s, NH, 2H), 4.10 (q, J=7 Hz, COOCH2CH3, 4H), 1.90 (t, J=7.2 Hz, CH2CONHOH, 4H), 1.71 (m, 4H), 1.45 (m, 4H), 1.18 (m, 8H), 1.14 (t, J=7 Hz, COOCH2CH3, 6H).

The compounds having the structure:

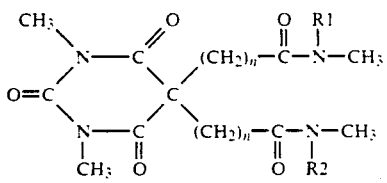

wherein R1 and R1 may independently be the same or different and is H or a lower alkyl group, wherein R3 and R4 may independently be the same or different and each is CH3 or OH, and wherein n is 5 or 6 were made as follows. 1,3-dimethylbarbituric acid (15.6 g; 0.1 mol) was slowly added at room temperature to a suspension of sodium hydride (4.8 g; 0.2 mol) in N,N-dimethylformamide (300 ml). The reaction was heated with stirring at 100° C. for about three hours. A DMF (200 ml) solution of benzyl 6-bromohexanoate (57 g; 0.2 mol) was slowly added to the cool suspension with vigorous stirring. The suspension was heated at 110° C. overnight, and the solvent was evaporated. The residue was partitioned between chloroform and water (300-300 ml). The chloroform layer was separated and the water layer was extracted with chloroform (5×50 ml). The combined chloroform layers were dried over anhydrous magnesium sulfate, and evaporated. The oily residue was purified by column chromatography on silica gel in ethyl acetate-tetrahydrofuran (9:1). The yield of dibenzyl ester was 18 g (32%).

The dibenzyl ester (18 g; 0.032 mol) was dissolved in methanol (50 ml) and catalyst (200mg of 5 % Pd-C) was added. The suspension was hydrogenated overnight, and the catalyst was removed by filtration. The methanol was evaporated yielding pure acid (11.5 g; 94%). The acid (11 g; 0.0286 mol) was suspended in benzene (500 ml), and oxalyl chloride (10 ml; 14.5 g; 0.14 mol) and a few drops of DMF were added. The mixture was stirred at room temperature for about 3 hours and evaporated to an oily residue. The oily residue was dissolved in chloroform (100 ml) and poured into a chloroform (100 ml) solution of O-benzyl-hydroxylamine (14.4 g; 0.117 mol). A white precipitate was formed immediately. After two hours stirring at room temperature the suspension was filtered. Concentrated hydrochloric acid (50 ml) was added to the filtrate and again filtered. The chloroform layer was separated and washed with concentrated hydrochloric acid (3×100 ml), water (3×100 ml) and dried over anhydrous magnesium sulfate. The chloroform was evaporated yielding pure N-benzyloxyamide (14 g; 82%).

The N-benzyloxyamide (6 g; 0.01 mol) was dissolved in methanol (509 ml) and catalyst (200 mg of 5% Pd-C) was added. The suspension was hydrogenated at room temperature overnight. The catalyst was removed by filtration and the methanol was evaporated yielding pure hydroxamic acid (3.95 g; 95%). The overall yield of 1,3-dimethyl-5,5-di(5-pentyl-n-hydroxylcaboxamide)barbituric acid was 23.4%.

$^1$H NMR (DMSO-d$_6$, 200 MHz), δ10.30 (s, OH, 2H), 8.60 (broad s, NH, 2H), 3.18 (s, N—CH3, 6H), 1.85 (t, J=7.2 Hz, CH2CONHOH, 4H), 1.80 (t, J=7 Hz, CH2-bar., 4H), 1.39 (m, 4H), 1.10 (m, 8H).

The compound having the structure:

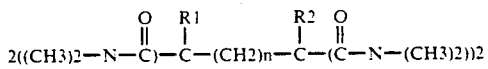

wherein R1 and R2 independently be the same or different and each may is H or a lower alkyl group and n is an integer from 1 to 10 is synthesized as follows. The tetramethylamide (2 g; 6.4 mmol; for n=2) in DMF (10 ml) was slowly added to a suspension of sodium hydride (0.9; 38 mmol) in DMF (50 ml). The mixture was stirred at 80° C. for about 30 minutes. Iodomethane (23.3 ml; 53.2 g; 380 mmol) was added to this cool solution at a temperature of about 5° C. and the reaction was continued at 60° C. overnight. The solvent was evaporated, and the residue was dissolved in water (50 ml). The water solution was extracted with 20% methanol in chloroform (10×30 ml). The combined organic extracts were dried over anhydrous magnesium sulfate and evaporated. The product was purified by short column chromatography in acetone. The yields of the alkane-1,1,n,n-tetra-(N,N-dimethylcarboxamide) were for: n=2, 1.3 g (55%); n=3 (52%); n=4, 51%; n=5 (53%); n=6 (53%).

$^1$H NMR (CDCl$_3$, 200 MHz) for compound having n=2, δ2.94 (s, N—Me, 12 H), 2.87 (s, N—Me, 12H), 1.82 (s, CH2, 4H), 1.32 (s, C-Me, 6H).

The compound having the structure:

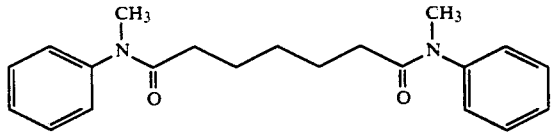

was synthesized as follows. N-methylanyline (7.3 ml; 7.219 g; 67.3 mmol) was slowly added to a solution of pimeloyl chloride (5 ml; 6.025 g; 30.6 mmol) in chloroform (500 ml). The suspension was stirred at room temperature for about three hours, and the solid was separated by filtration. The chloroform filtrate was washed with concentrated hydrochloric acid (3×100 ml), water (3×100 ml) and dried over anhydrous magnesium sulfate. The chloroform was evaporated, the solid residue was slurried in hexanes and filtered. The yield of pentane-1,5-di(N-methyl-N-phenylcarboxamide) was 6.3 g (90%).

¹H NMR (DMSO—d₆, 200 MHz). δ7.30 (m, Ph, 10 H), 3.12 (s, N—Me, 6H), 1.93 (t, J=7 Hz, CH2CON, 4H), 3.31 (m, 4H), 1.01 (m, 2H).

The compound having the structure:

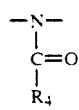

was synthesized as follows. To a suspension of sodium hydride (0.24 g; 0.01 mol) in DMF (30ml) at room temperature was added slowly to aniline (1 ml; 1 g; 10.7 mmol) in DMF (5 ml) The mixture was heated at 110° C. for three hours. Diethyl di(N,N-dimethylpentamethylenecarboxamide)malonate (4.42 g; 0.01 mol) in DMF (10 ml) was added to the cool reaction mixture. The mixture was stirred at 110° C. overnight. The solvent was evaporated. The residue was partitioned between water and chloroform (100–100 ml). The chloroform layer was separated, and the water layer was extracted with 4:1 chloroform-methanol (5×50 ml). The combined organic layers were dried over anhydrous magnesium sulfate and evaporated to an oily residue. The product was purified by column chromatography on silica gel in tetrahydrofuran. The yield of undecane-1,11-di(N,N-dimethyl-carboxamide)-6-ethoxycarbonyl-6-(N-phenylcarboxamide) was 2.1 g (43%).

¹H NMR (CDCl3, 200 MHz), δ7.59 (d, J=7.4 Hz, arom. 2H), 7.28 (t, J=7.4 Hz, arom. 2H), 7.26 (s, NH, 1H), 7.10 (t, J=7.4 Hz, arom. 1H), 4.26 (q, J=7 Hz, COOCH2CH3, 2H), 2.99 (s, N—Me, 6H), 2.95 (s, N—Me, 6H), 2.24 (t, J=5.2 Hz, CH2CON, 4H) 1.85 (m, 4H), 1.60 (m, 4H), 1.65 (m, 8H).

The compounds having the structure:

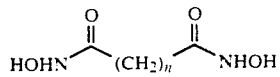

were made as follows. A solution of suberoyl chloride (n=6; 10 ml; 11.72 g; 55.5 mmol) in tetrahydrofuran (50 ml) Was slowly added (about 1 hour) to a stirred solution of potassium hydroxide (12.4 g; 22.2 mmol) and hydroxylamine hydrochloride (7.72 g; 111 mmol) in water (200 ml), maintaining the reaction temperature below 5° C. The reaction suspension was stirred an additional two hours at room temperature. The white precipitate (where n=6–11) was filtered and the filtrate was washed with cold water (5×20 ml), acetone (5×20 ml) and ether (3×50 ml). The product was more than 95% pure by NMR(DMSO). The product can be purified by crystallization from acetone. When n=2–5, the reaction mixture was evaporated. The white crystals were slurried in hot methanol (about 1 liter) and filtered. The filtrate was dried over anhydrous magnesium sulfate and the methanol was evaporated. The white crystals were purified by crystallization from methanol or acetone. The yields of alkane-1,n-di(N-hydroxylcarboxamide) were for n=2, 57%; n=3, 64%; n=5, 71%; n=6, 63%; n=7, 68%; n=8, 78%; n=9, 75%; n=10; 79%; and n=1, 81%.

The compound having the structure:

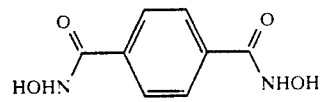

was synthesized as follows. A solution of tetraphthaloyl chloride (5 g; 24 mmol) in tetrahydrofuran (50 ml) was slowly added (about 30 minutes) to a stirred solution of potassium hydroxide (5.52 g; 98.6 mmol) and hydroxylamine hydrochloride (3.4 g; 48.9 mmol) in water (100 ml) and the reaction was maintained at a temperature below 5° C. The reaction suspension was stirred an additional hour at room temperature. The suspension was evaporated, and the solid was slurried in boiling methanol (about 1 liter). The hot methanol suspension was filtered, the filtrate was dried over anhydrous magnesium sulfate and the methanol was evaporated. The solid residue was slurried in ethyl acetate (30 ml). The solid was separated by filtration and washed with ether (5×10 ml) and hexanes (5×10 ml). The yield of benzene-1,4-di(N-hydroxylcarboxamide) was 3.2 g; (66%).

The compound having the structure:

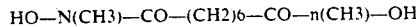

was made by slowly adding a solution of suberoyl chloride (5 g; 23.7 mmol) in tetrahydrofuran (20 ml) to a stirred water solution of potassium hydroxide (5.3 g; 94.8 mmol) and N-methylhydroxylamine hydrochloride (4 g; 47.4 mmol) at about 5° C. The reaction mixture was stirred at room temperature for about one hour. The organic layer was separated and the water layer was extracted with chloroform (5×50 ml). The combined chloroform layers were dried over anhydrous magnesium sulfate and evaporated. The product was purified by crystallization from acetone. The yield of hexane-1,6-di(N-hydroxyl-N-methylcarboxamide was 2.7 g (46%).

Each compound in Table 1 was assayed 3 or more times to determine effectiveness as an inducer of MELC (745A-DS19) cell line. The cell density of MELC in culture for 5 d. without inducer was 2.0 to $2.6 \times 10_6$ cells/ml. The cell density of MELC in culture for 5 d. with inducer was 1.2 to $2.0 \times 10_6$ cells/ml. Compounds 11 and 12 were dissolved in absolute ethyl alcohol. The final concentration of ethyl alcohol in the cultured medium ranged between 0.1 and 3%. This concentration of ethyl alcohol had no effect on cell growth of MELC in culture without inducer. All other compounds were dissolved in culture medium without fetal calf serum. The indicated optimal concentration represents the final concentration in the culture medium.

RESULTS

New Hybrid Polar/Apolar Compounds Active as Cytodifferentiation Agents

In earlier studies (8), the present inventors reported that fairly high concentrations of certain polar organic solvents induce MELC to undergo erythroid differentiation. The question arose as to how the effectiveness of polar compounds might be increased so that similar concentrations of these solvent-like molecules could induce differentiation. Although the mechanisms were not clear, and are still incompletely understood, the following hypothesis was considered: perhaps, at the target site of action, more than one solvent molecule must bind or interact. If this were so, the well-known chelate effect could provide more effective compounds. Instead of binding two or more independent solvent molecules, the cellular target might interact more efficiently with a single molecule carrying two or more solvent-like groups. Provided these groups were held in the right relationship one to the other, binding of one would carry the other into the target region providing a high, effective concentration. Such a chelate effect is well precedented; it accounts for the strong binding of metal ions by chelating ligands, and is the basis for much of the catalytic activity of enzyme.

This concept led the present inventors to new effective cytodifferentiating agents. The best studied to date is hexamethylene bisacetamide (HMBA, Table 1, compound 1), consisting of two acetamide molecules linked at nitrogen by a six carbon polyethylene chain (5,9). N-methyl acetamide (Table 1, compound 2), another of the polar organic solvents, was shown to be effective, but only at high concentration (50 mM), whereas HMBA induces erythroid differentiation in MELC at an optimal concentration of 5 mM (8). The present inventors previously showed that the optimum number of methylene groups in the apolar chain is six (27). In the present invention, it was found that a four or five carbon chain is comparably effective if extra carbons are provided as branching methyl groups (Table 1, compounds 3, 4 and 5). This suggests that the important factor is not simply the length of the chain but also the number of hydrophobic hydrocarbon units in it.

Acetamide can also be dimerized by linking the methyl groups of the molecule. Suberic acid bis-N-methylamide (SBDA; Table 1, compound 7), can be thought of as N-methylacetamide linked at the acetyl group by four methylene units. SBDA is comparable in activity as an inducer to HMBA (FIG. 1A and B). Since the structures of SBDA and HMBA are different, it is likely that the metabolic fates of these two compounds are completely different, and their similarity in effectiveness means that the compounds themselves are the principal active agents, rather than their catabolic products.

Figure 1C:
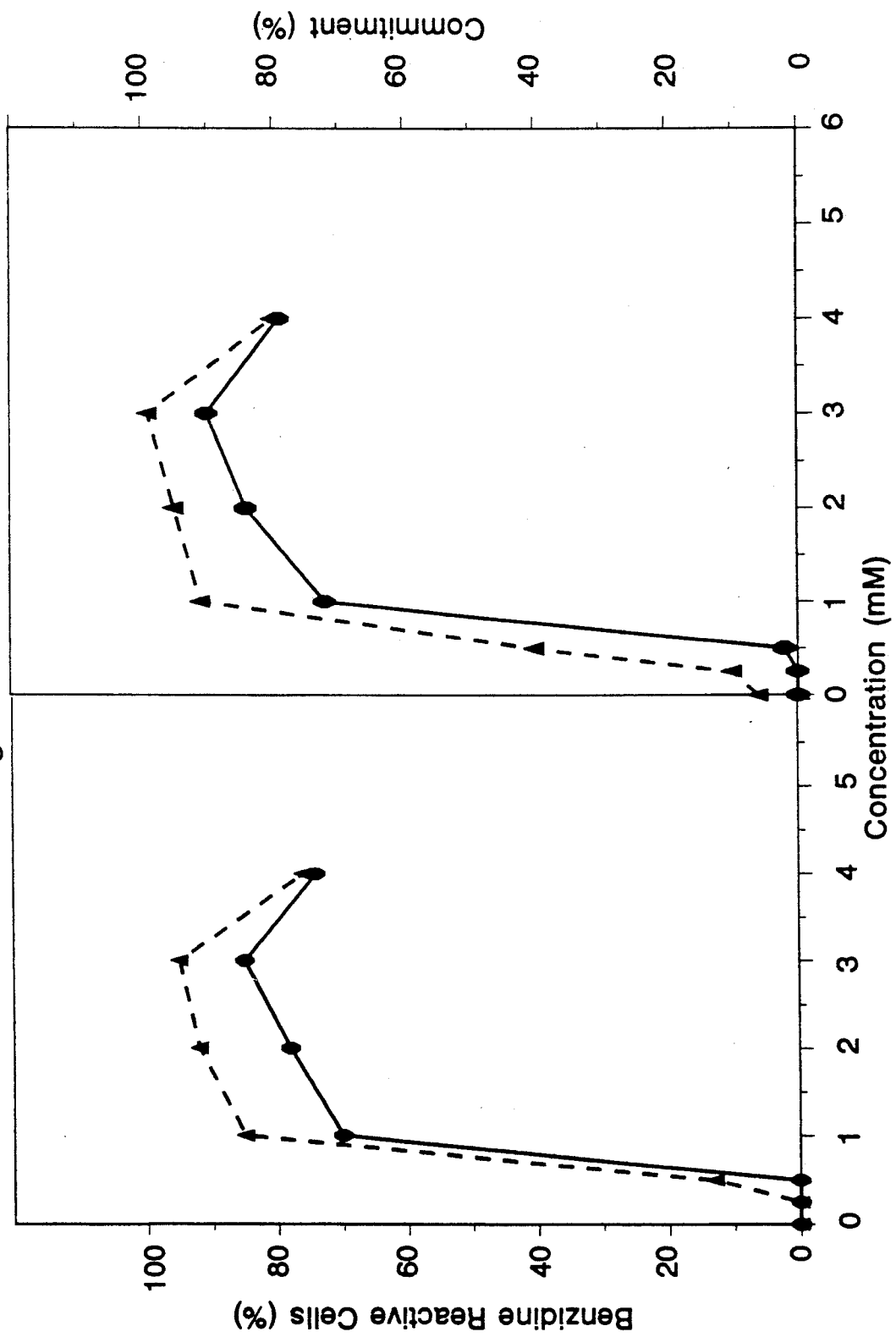
Figure 2:
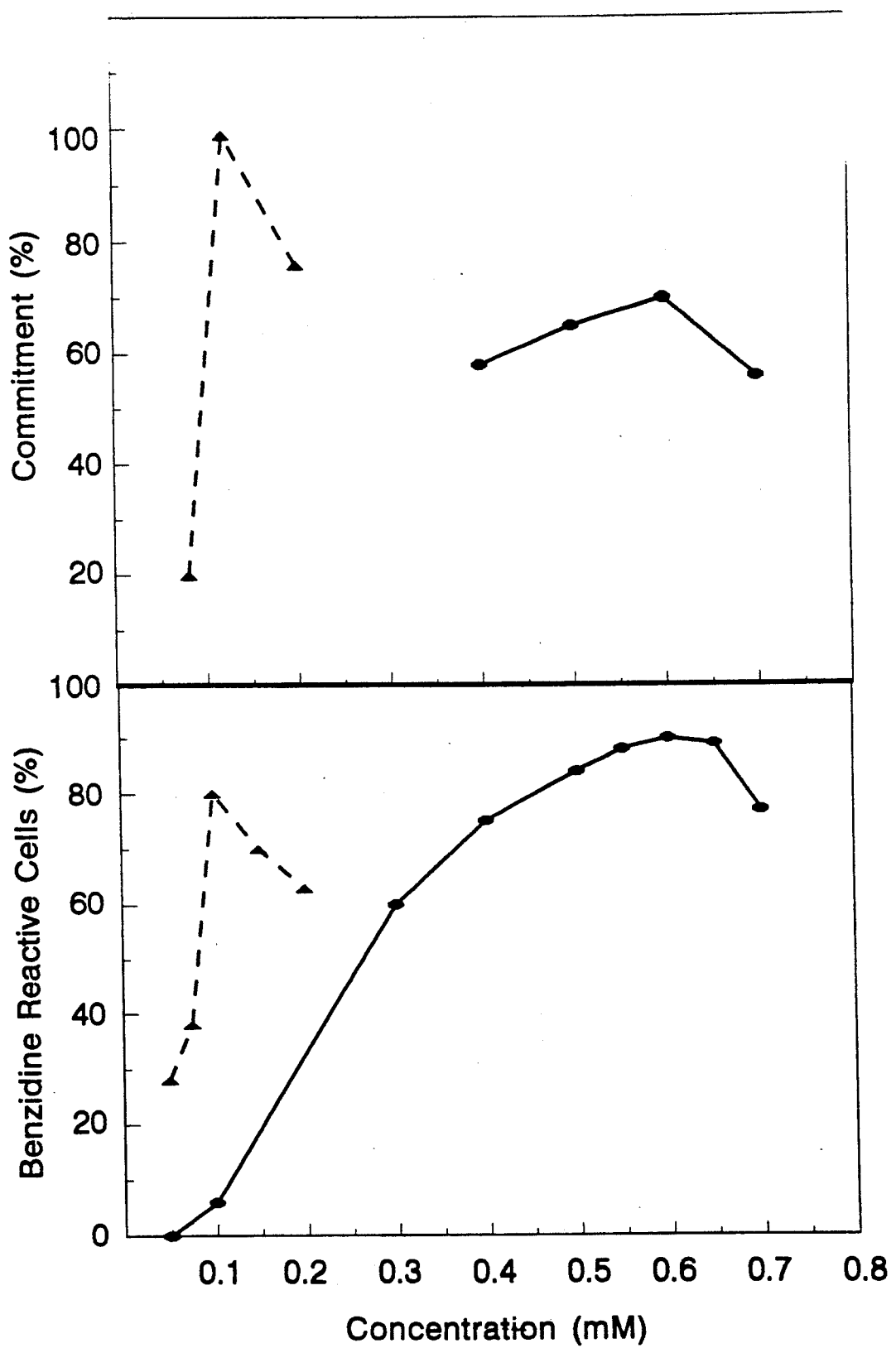
FIG. 2: Concentration dependent curves of inducer activity of compound 12 with vincristine-sensitive (745A-DS19) (●) and vincristine-resistant (VCR.C(2)15) (▲) MELC. The compound was added to the cultures at the final concentrations indicated. Benzidine reactive cells were determined after 5 d. in culture and commitment after 2 d. of culture.

HMBA and SBDA have their polar groups separated by identical methylene bridges, and they have a similar ratio of polar to apolar hydrophobic moieties. Many structurally related compounds have been examined, but only a few showed comparable or greater activity (Table 1, compounds 6 through 12). It is clear that the structures of active compounds may differ sufficiently from HMBA to make it likely that they will also display different pharmacokinetics. One of the more active of these hybrid compounds is a dimmer of HMBA. Bishexamethylene triacetamide (BHTA; compound 10) is about 2 fold more active as inducer, on a molar basis, than HMBA (FIG. 1C). The most active of the hybrid compounds assayed in this study is one in which two pentamethylene carboxyamides are linked by the dimethyl ester of malonic acid (compound 12). This compound, with 4 exposed polar groups balanced by two apolar pentamethylene domains, is roughly 10 fold more active than HMBA. For example, 0.6 mM compound 12 is about as effective as 5.0 mM HMBA, inducing over 90% of cells to differentiate after 5 d. in culture (FIG. 2).

Polymethylenediamine derivatives carrying propionyl groups instead of the acetyl groups of HMBA are also active, but methoxycarbonyl groups are less effective and bulky pivaloyl groups lead to loss of activity. The present inventors previously showed that HMBA can have a double bond (cis or trans) or a triple bond in the center and retain its activity (27). Replacement of the polymethylene chain with a cyclohexane ring leads to inactivity (27), although compound 9, with a longer chain interrupted by an amide group, is active.

Diamides of dicarboxylic acids, such as suberic acid, are active with either one or two methyl groups on each nitrogen (compounds 7, 8, and 9), but not with a methyl and a methoxyl substituent, and they are also active with one (but not two) ethyl groups on each nitrogen. Suberic diamides of pyrollidine, of morpholine, or of piperazine are inactive. This shows that there is a limit to the amount of carbon tolerated on the ends of the polar groups.

These findings indicate that for optimal activity, two, or even better, three or four uncharged polar groups of limited bulk must be connected by chains of about 5 to 6 carbons.

Increased Sensitivity of Vincristine-Resistant MELC to Polar/Apolar Compounds

As previously reported, MELC resistant to relatively low concentrations of vincristine show a marked increase in sensitivity to HMBA (FIG. 1A) (26). The dose-response of MELC to several of the new polar compounds identified as being as or more active than HMBA was examined. The compounds assayed for inducing activity with vincristine-resistant MELC include compounds 1, 3, 4, 8, 10, 11 and 12 (Table 1). In each instance, vincristine-resistant MELC were induced at lower concentrations than were required for induction of vincristine-resistant MELC were induced more rapidly than the vincristine-sensitive cells. For the most active of the compounds, 0.1 mM compound 12 was the optimal concentration for inducing vincristine-resistant MELC (VCR.C(2)15). For example, 0.1 mM compound 12 induced only 6% commitment of over 95% of V.C.R.(2) 15 cells after 2 d. and the accumulation of over 80% benzidine-sensitive (DS-19) MELC, 0.1 mM compound 12 induced only 6% commitment by d. 2 and 4% benzidine reactive cells by d. 5. At concentrations of compound 12 as low as 0.05, 35% of VCR.C(2)15 became benzidine reactive by d. 2, compared to only 2% of DS-19.

Effect of Polar/Apolar Compounds on MELC Resistant to Inducer Mediated Terminal Cell Division Several of the new polar/apolar compounds were evaluated as inducers of MELC cell line DR10, which is resistant to induction by dimethylsulfoxide and can be induced by HMBA to accumulate hemoglobin but not commit to terminal cell division (37). Compounds 7, 8 and 10, assayed as inducers of DR10, caused accumulation of hemaglobin, but not commitment to terminal cell division. Thus, these new hybrid polar/apolar compounds are similar to HMBA in their effect on DR10 cells.

Cell cultures were grown in the presence of different concentrations of Hexamethylenebisacetamide (HMBA)

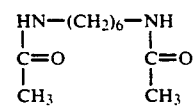

and compound 10, bis-Hexamethylenetriacetamide (IC-135).

Figure 3B:
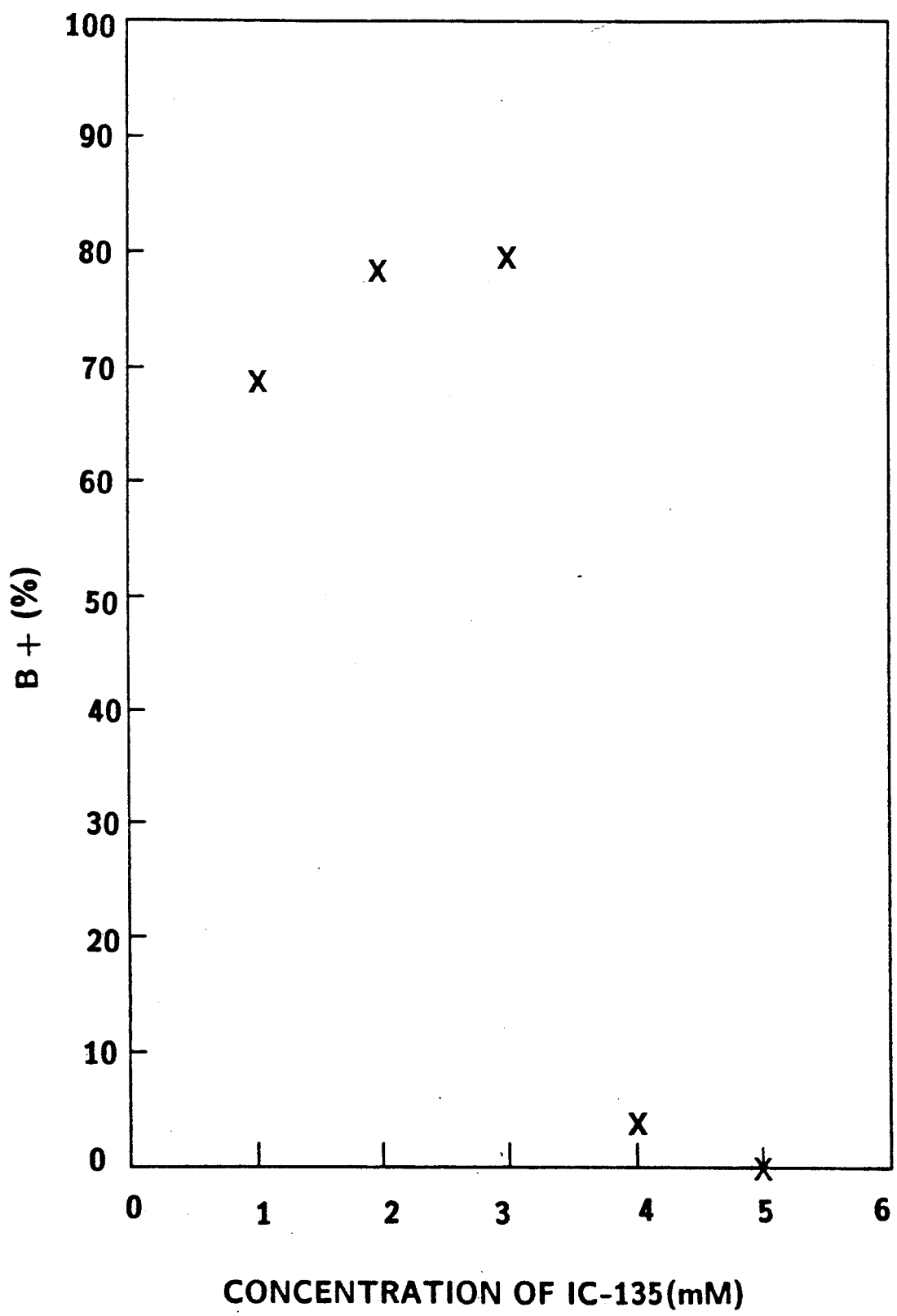
FIG. 3: Optimal concentration of IC-135 for inducement of terminal differentiation.
Figure 4:
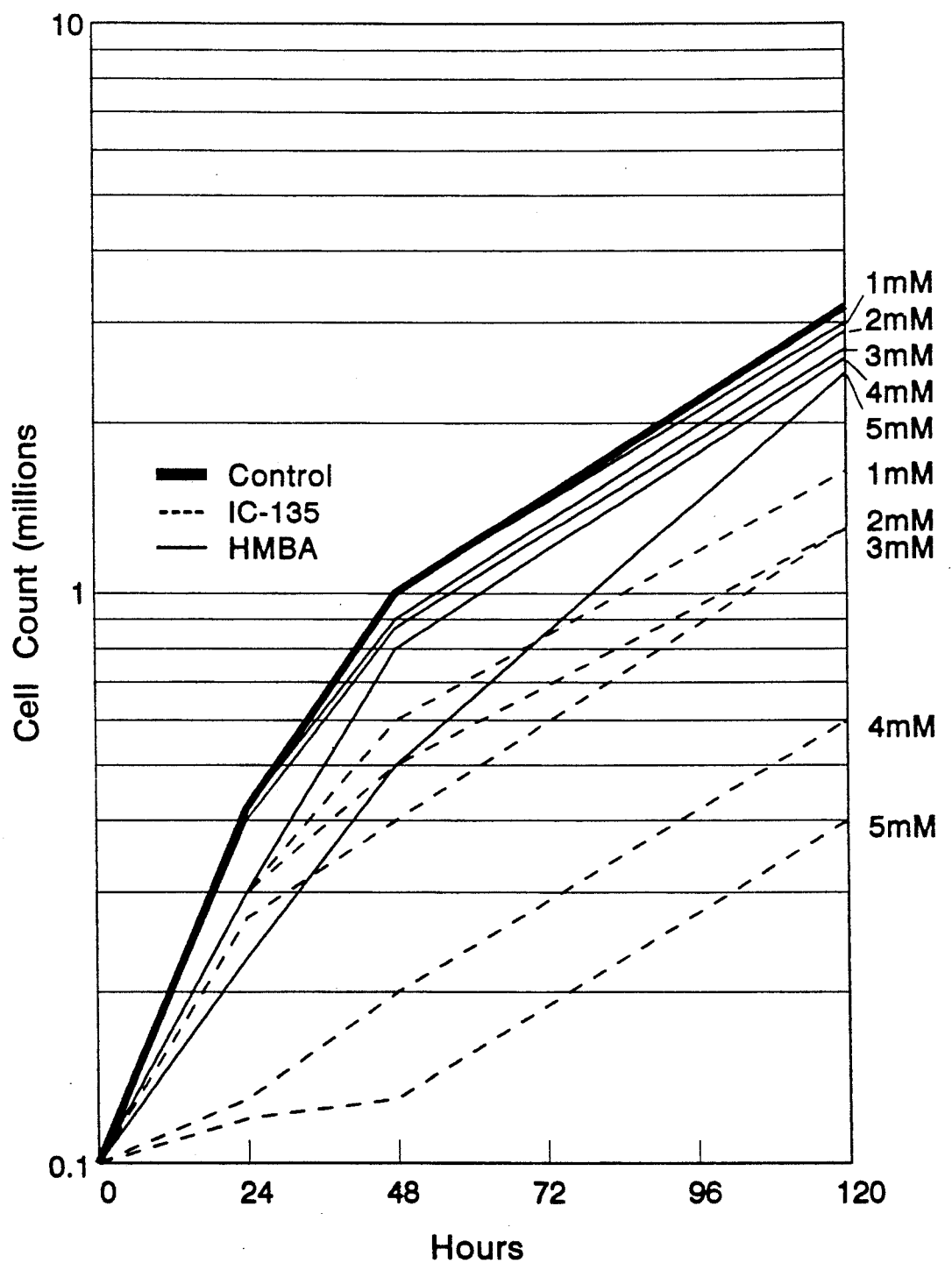
FIG. 4: Comparison of HMBA and IC-135 on DS19 cells.
Figure 5A:
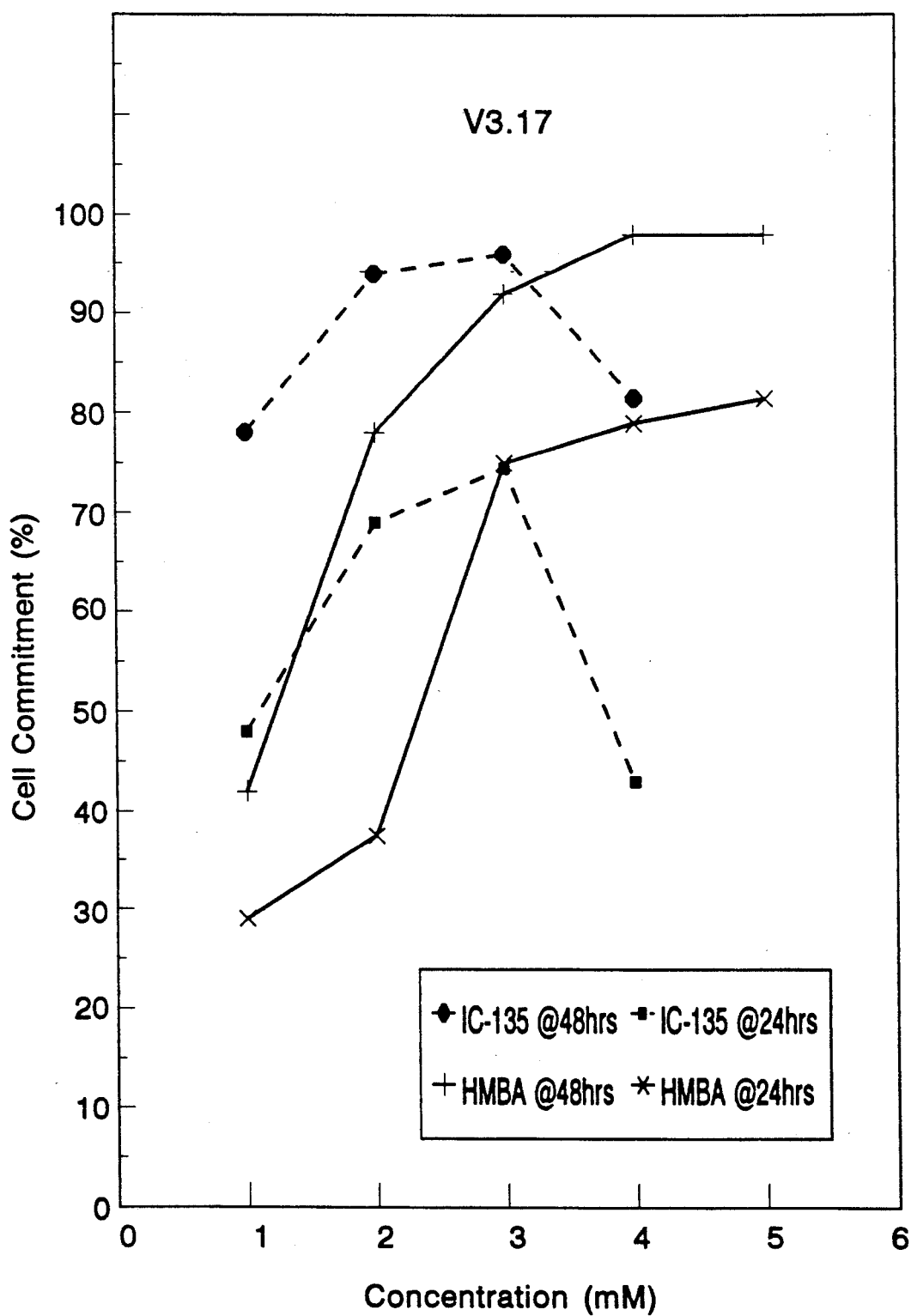
FIG. 5A and B: Comparison of % cell committed for HMBA and IC-135 on V3.17 and DS19 cell lines.
Figure 5B:
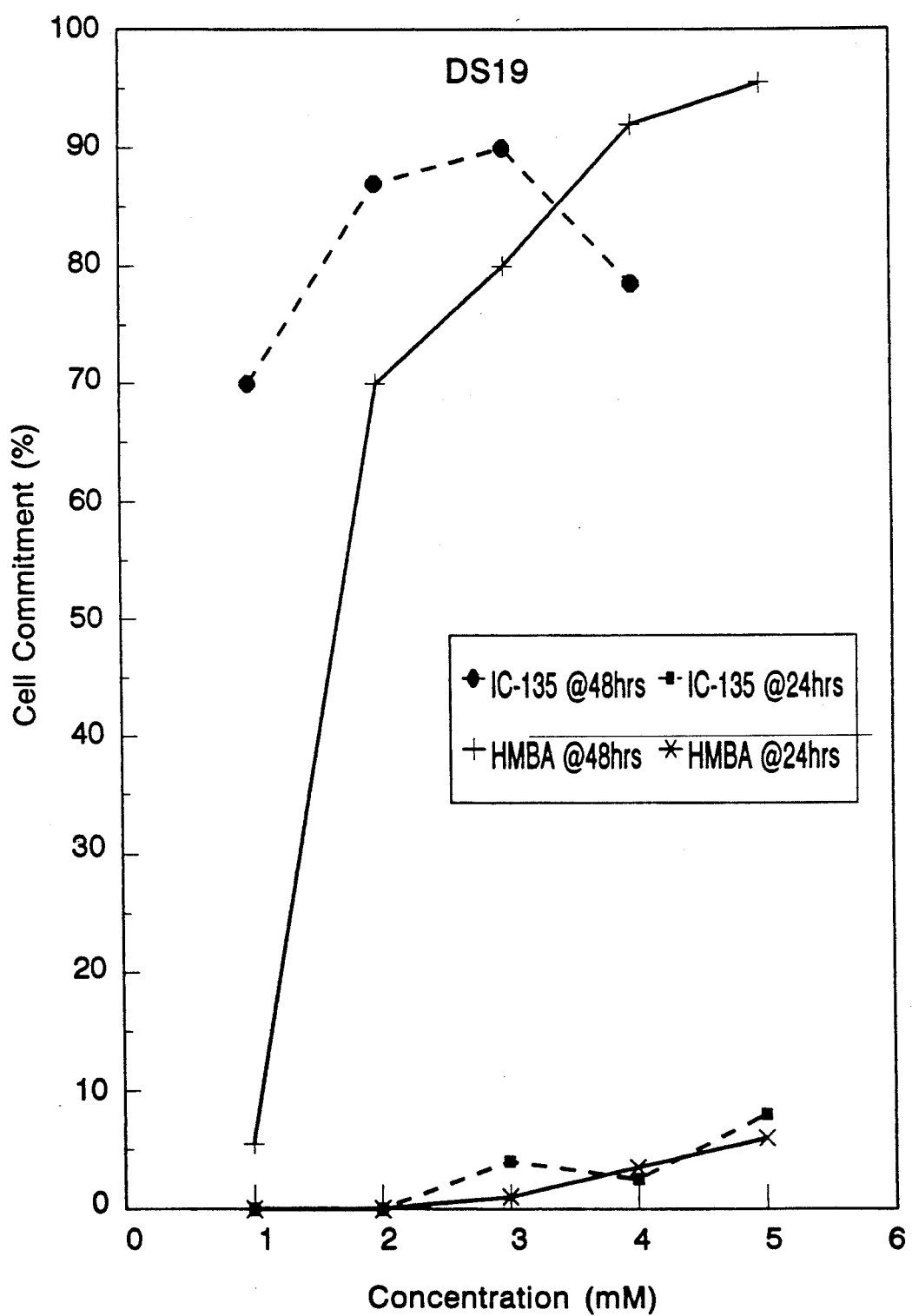
Figure 6A:
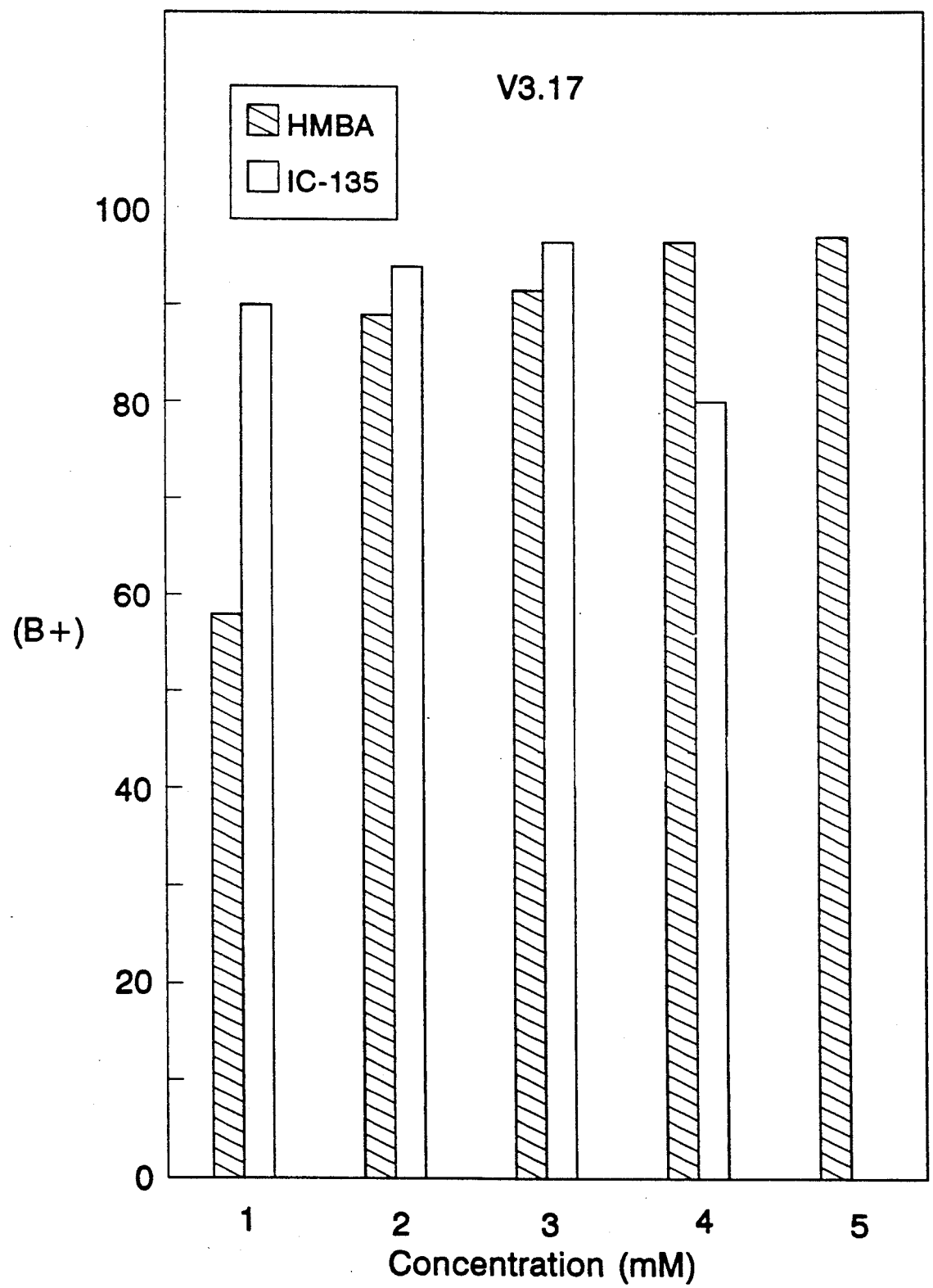
FIG. 6A and B: Comparison of B+% for HMBA and IC-135 on V3.17 and DS19 cell lines.
Figure 6B:
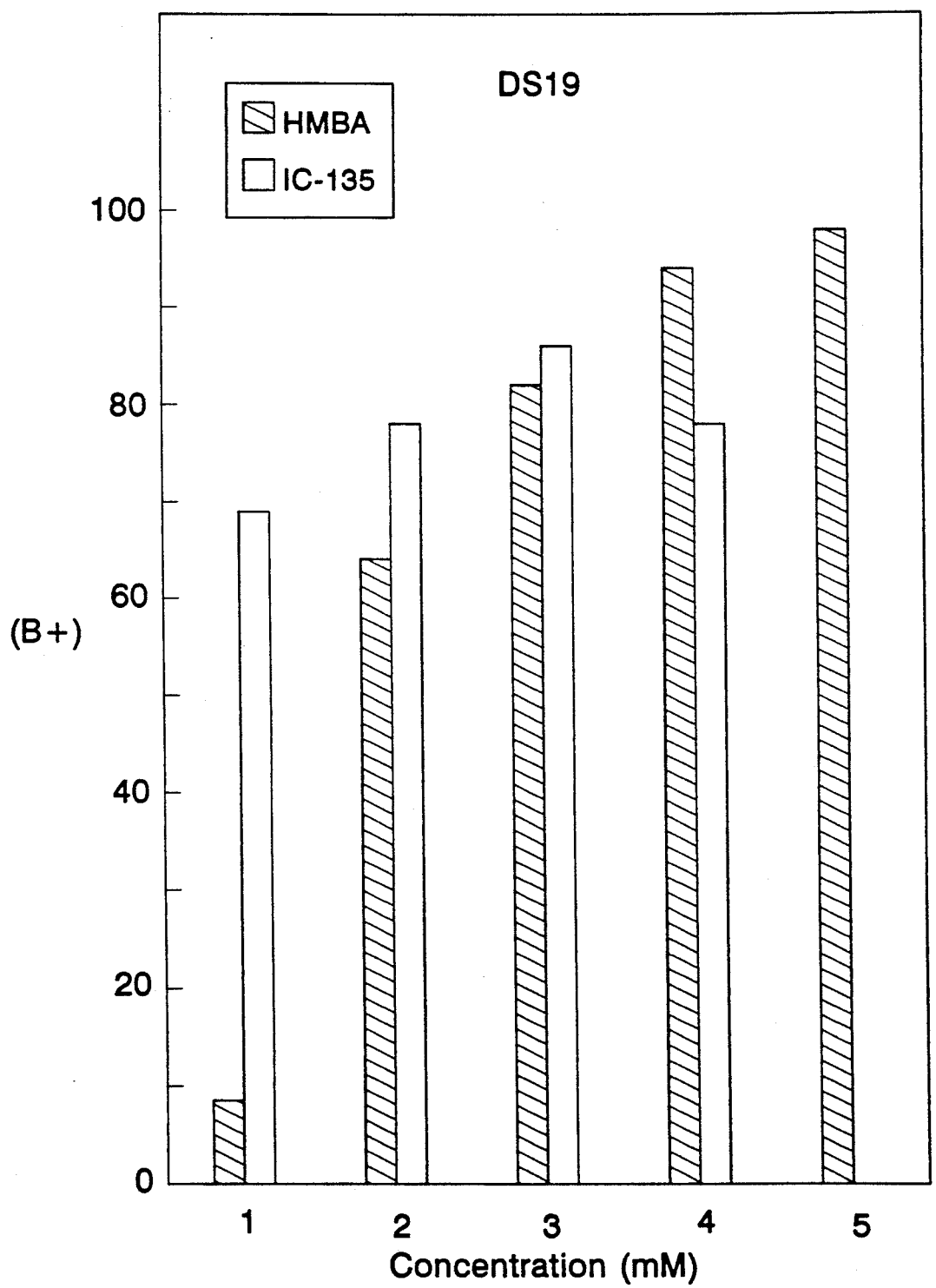

At 1, 2 and 5 days, the cell densities and the percentage of cells that were benzidine reactive (B+) were measured. Table 2 shows the cell densities, B+%, and percent of cells committed for cell lines DS19 and V3.17 grown in 1 mM to 5 mM of HMBA and IC-135. FIGS. 3, 4, 5A and B, and 6A and B are graphical representations of the data presented in Table 2.

Table 3 shows cell counts for days 1, 2 and 5 and percentage of cells committed and benzidine reactive (B+) at day 5 for cell liens DS-19, V3.17 and DR-10 grown in 5 mM of HMBA and 0.5 to 3 mM of IC-135.

As can be seen in Table 2 and 3 and FIGS. 3-6, IC-135 is more reactive in the tested cell lines at lower concentrations than HMBA.

Table 4 shows the results of several structurally different compounds when assayed 3 or more times to determine effectiveness as an inducer of MELC (745A-DS19) cell line. The cell density of MELC in culture for 5 d. without inducer was 2.0 to $2.6 \times 10_6$ cells/ml.

DISCUSSION

The development of agents which can induce transformed cells to differentiate and suppress their oncogenicity has important implications for the treatment of cancer. While a number of agents have been identified that can induce tumor cells in vitro to express features of their differentiated phenotype and to decrease their proliferative capacity (4,10-24), these agents have generally proved to be relatively ineffective or two toxic when evaluated in clinical trials (40).

Among cytodifferentiation agents, the hybrid polar-/apolar compound, HMBA, has been one of the best characterized with respect to its in vitro inducing activity in MELC and in a number of other transformed cell lines, as well as for certain human tumor explants (30). It can trigger a differentiation program in transformed cells which is similar to that of their normal lineage (5).

The recent finding that vincristine-resistant MELC are more sensitive to HMBA and to other active hybrid polar/apolar compounds provides an approach toward identifying the mechanisms of HMBA action (26). The lack of a latent period for inducer-mediated differentiation of vincristine-resistant cells suggests that an early effect of inducers may involve alternations (e.g. new proteins, or modification of existing proteins such as phosphorylation) which are constitutively expressed in the vincristine-resistant cell lines, and may, therefore, be identified and characterized.

The observed positive therapeutic responses to HMBA, albeit largely transient, occurred despite relatively low serum concentrations of HMBA (<1 mM), compared to the optimum demonstrated in vitro (4 to 5 mM) (35,36). The present invention provides a new group of hybrid polar/apolar compounds which are as active or even more active, on a molar basis, than HMBA.

TABLE 4

| CPD | Structure | | Mol. Weight | Optimal Concentration ($\mu$M) | Benzidine Reactive Cells (%) | Commitment (%) |
|---|---|---|---|---|---|---|
| | HO—N(H)—C(=O)—(CH$_2$)$_n$—C(=O)—N(H)—OH | | | | | |
| 13. | | n = 2 | 148 | 0 | | |
| 14. | | n = 3 | 162 | 0 | | |
| 15. | | n = 4 | 176 | 300 | 60 | |
| 16. | | n = 5 | 190 | 40 | 89 | |
| 17. | | n = 6 | | | | |
| 18. | | n = 7 | 218 | 20 | 75 | |
| 19. | | n = 8 | 232 | 20 | 38 | |
| 20. | | n = 9 | 246 | 20 | 20 | |
| 21. | | n = 10 | 260 | 20 | 26 | |
| 22. | | n = 11 | 274 | 20 | 9 | |
| 23. | HO—N(H)—C(=O)—C$_6$H$_4$—C(=O)—N(H)—OH | | 196 | 80 | 88 | |
| 24. | HOHN—C(=O)—C$_6$H$_4$—CH=CH—C(=O)—NHOH | | | 5 | 64 | |
| 25. | (CH$_3$)(O=C—N)—C(=O)—(CH$_2$)$_5$—C(=O)—N(CH$_3$)$_2$ cyclic dimer structure | | 438 | 600 | 95% | |

TABLE 4-continued

| CPD | Structure | Mol. Weight | Optimal Concentration (μM) | Benzidine Reactive Cells (%) | Commitment (%) |
|---|---|---|---|---|---|
| 26. | (structure) | 424 | 500 | 19% | |
| 27. | (structure) | 311 | 5000 | 85 | |
| 28. | (structure) | 414 | 600 | 85 | |
| 29. | (structure) | 442.60 | 600 | 95 | |

REFERENCES:

1. Sporn, M.B., Roberts, A.B., Driscoll, J.S. (1985) in *Cancer: Principles and Practice of Oncology*, eds. Hellman, S., Rosenberg, S.A. & DeVita, V.T., Jr., Ed. 2, (J.B. Lippincott, Philadelphia), P. 49.
2. Breitman, T.R., Selonick, S.E., and Collins, S.J. Induction of differentiation of the human promyelocytic leukemia cell line (HL-60) by retinoic acid. *Proc. Natl. Acad. Sci. USA.*, 77:2936–2940, 1980.
3. Olsson, I.L., and Breitman, T.R. Induction of differentiation of the human histiocytic lymphoma cell line U.937 by retinoic acid and cyclic adenosine 3':5'-monophosphate-inducing agents. *Cancer Res.*, 42:3924–3927, 1982.
4. Schwartx, E.G. & Sartorelli, A.C. (1982) *Cancer Res.*, 42, 2651–2655.
5. Marks, P.A., Sheffery, M. & Rifkind, R.A. (1987) *Cancer Res.* 47, 659.
6. Sachs, L. (1978) *Nature (Lond.)* 274, 535.
7. Friend, C., Scher, W., Holland, J.W. & Sato, T. (1971) *Proc. Natl. Acad. Sci. (USA)*, 68, 378–382.
8. Tanaka, M., Levy, J., Terada, M., Breslow, R., Rifkind, R.A. & Marks, P.A. (1975) *Proc. Natl. Acad. Sci. (USA)*, 72, 1003–1006.
9. Reuben, R.C., Wife, R.L., Breslow, R., Rifkind, R.A. & Marks, P.A. (1976) *Proc. Natl. Acad. Sci. (USA)*, 73, 862–866.
10. Abe, E., Miyaura, C., Sakagami, H., Takeda, M., Konno, K., Yamazaki, T., Yoshika, S. & Suda, T. (1981) *Proc. Natl. Acad. Sci. (USA)*, 78, 4990–4994.
11. Schwartz, E.L., Snoddy, J.R., Kreutter, D., Rasmussen, H. & Sartorelli, A.C. (1983) *Proc. Am. Assoc. Cancer Res.*, 24, 18.
12. Tanenaga, K., Hozumi, M. & Sakagami, Y. (1980) *Cancer Res.*, 40, 914–919.
13. Lotem, J. & Sachs, L. (1975) *Int. J. Cancer.* 15, 731–740.
14. Metcalf, D. (1985) *Science*, 229, 16–22.
15. Scher, W., Scher, B.M. & Waxman, S. (1983) *Exp. Hematol.*, 11, 490–498.
16. Scher, W., Scher, B.M. & Waxman, S. (1982) *Biochem. & Biophys. Res. Comm.*, 109, 348–354.
17. Huberman, E. & Callaham, M.F. (1979) *Proc. Natl. Acad. Sci. (USA)*, 76, 1293–1297.
18. Lottem, J. & Sachs, L. (1979) *Proc. Natl. Acad. Sci. (USA)*, 76, 5158–5162.
19. Terada, M., Epner, E., Nudel, U., Salmon, J., Fibach, E., Rifkind, R.A. & Marks, P.A. (1978) *Proc. Natl. Acad. Sci. (USA)*, 75, 2795–2799.
20. Morin, M.J. & Sartorelli, A.C. (1984) *Cancer Res.*, 44, 2807–2812.
21. Schwartz, E.L., Brown, B.J., Nierenberg, M., Marsh, J.C. & Sartorelli, A.C. (1983) *Cancer Res.*, 43, 2725–2730.
22. Sugano, H., Furusawa, M., Kawaguchi, T. & Ikawa, Y. (1973) *Bibl. Hematol.*, 39, 943–954.
23. Ebert, P.S., Wars, I. & Buell, D.N. (1976) *Cancer Res.*, 36, 1809–1813.
24. Hayashi, M., Okabe, J. & Hozumi, M. (1979) *Gann*, 70, 235–238.
25. Fibach, E., Reuben, R.C., Rifkind, R.A. & Marks, P.A. (1977) *Cancer Res.*, 37, 440–444.

26. Melloni, E., Pontremoli, S., Damiani, G., Viotti, P., Weich, N., Rifkind, R.A. & Marks, P.A. (1988) *Proc. Natl. Acad. Sci.* (USA), 85, 3835-3839.

27. Reuben, R., Khanna, P.L., Gazitt, Y., Breslow, R., Rifkind, R.A. & Marks, P.A. (1978) *J. Biol. Chem.*, 253, 4214-4218.

28. Marks, P.A. and Rifkind, R.A. Hexamethylene Biscetamide Induced Differentiation of Transformed Cells: Molecular and Cellular Effects and Therapeutic Application. International Journal of Cell Cloning, 6:230-240, 1988.

29. Melloni, E., Pontremoli, S., Michetti, M., Sacco, O., Cakiroglu, A.G., Jackson, J.F., Rifkind, R.A. & Marks, P.A. *Proc. Natl. Acad. Sciences* (USA) 84, 5282-5286, 1987.

30. Marks, P.A. & Rifkind, R.A. (1984) *Cancer*, 54, 2766-2769.

31. Egorin, M.J., Sigman, L.M. VanEcho, D.A., Forrest, A., Whitacre, M.Y. & Aisner, J. (1987) *Cancer Res.*, 47, 617-623.

32. Rowinsky, E.W., Ettinger, D.S., Grochow, L.B., Brundrett, R.B., Cates, A.E. & Donehower, R.C. (1986) *J. Clin. Oncol.*, 4, 1835-1844.

33. Rowinsky, E.L. Ettinger, D.S., McGuire, W.P., Noe, D.A., Grochow, L.B. & Donehower, R.C. (1987) *Cancer Res.*, 47, 5788-5795.

34. Callery, P.S., Egorin, M.J., Geelhaar, L.A. & Nayer, M.S.B. (1986) *Cancer Res.*, 46, 4900-4903.

35. Young, C.W. Fanucchi, M.P., Walsh, T.B., Blatzer, L., Yaldaie, S., Stevens, Y.W., Gordon, C., Tong, W., Rifkind, R.A. & Marks, P.A. (1988) *Cancer Res.*, 48, 7304-7309.

36. Andreeff, M., Young, C., Clarkson, B., Fetten, J., Rifkind, R.A. & Marks, P.A. (1988) *Blood*, 72, 186a.

37. Ohta, Y., Tanaka, M., Terada, M., Miller, O.J., Bank, A., Marks, P.A. & Rifkind, R.A. (1976) *Proc. Natl. Acad. Sci.* (USA) 73, 1232-1236.

38. Cartledge, F.K. & Nguyen, T.B. (1986) *J. Org. Chem.*, 51, 2206-2210.

39. Hoffmann-LaRoche and Co., A.G. British Patent 1, 138-529 (1969).

40. Dmitrovsky, E., Markman, M. & Marks, P.A. (1989) in *Cancer Chemotherapy and Biological Therapy*, Annual 11, eds., D.L. Longo, H.M. Pinedo, B.A. Chabner, eds., Excepta Medica, Publisher, in press.

What is claimed is:

1. A method of selectively inducing terminal differentiation of neoplastic cells and thereby inhibiting proliferation of such cells which comprises contacting the cells under suitable conditions with an amount of a compound effective to selectively induce terminal differentiation, the compound having the structure:

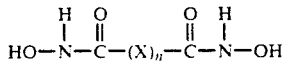

wherein X is phenyl and n is an integer from 1 to 5.

2. A method of clam 1, wherein the effective amount of the compound is from about 2 μM to about 6000 μM.

3. A method of claim 2, wherein the contacting is effected continuously for at least 48 hours.

* * * * *

UNITED STATES PATENT AND TRADEMARK OFFICE
CERTIFICATE OF CORRECTION

PATENT NO. : 5,175,191

DATED : December 29, 1992

INVENTOR(S) : Paul A. Marks, et al.

It is certified that error appears in the above-identified patent and that said Letters Patent is hereby corrected as shown below:

On the title page, following [73] Assignees, "Sloan-Kettering Institute for Cancer Research; The Trustees of Columbia University Institute for Cancer Research in the City of New York" should read --Sloan-Kettering Institute for Cancer Research; The Trustees of Columbia University in the City of New York--.

On the title page, following [30] Foreign Application Priority Data, please delete "Nov. 14, 1989 [WO] World Int. Prop. O. .............PCT/US89/05203".

On the title page, item [57], in the Abstract, line 6, "termini" should read --terminal--.

On the title page, item [57], in the Abstract, line 8, "condition" should read --conditions--.

Column 2, lines 58-59, "$[R-A]-B-A_1-B_1-[A_2-B_2]_a[A_3-B_3]_b-[A_4[A_4-R_1]$" should read --$[R-A]-B-A_1-B_1-[A_2-B_2-]_a[A_3-B_3]_b-[A_4-R_1]$--.

Column 3, line 18, "$A_3$ and $A_4$ and respectively" should read- --$A_3$ and $A_4$, respectively--.

Column 6, line 13, "CH3 or OH" should read --$CH_3$ or OH--.

Column 6, line 63, "condition" should read --conditions--.

Column 8, line 18, "a amine" should read --an amine--.

Column 8, line 54, "a ethyl" should read --an ethyl--.

Column 11, line 10, "H or CH3" should read --H or $CH_3$--.

Column 12, line 20, "R1 and R1" should read --R1 and R2--.

UNITED STATES PATENT AND TRADEMARK OFFICE
CERTIFICATE OF CORRECTION

PATENT NO. : 5,175,191

DATED : December 29, 1992

INVENTOR(S) : Paul A. Marks., et al.

It is certified that error appears in the above-identified patent and that said Letters Patent is hereby corrected as shown below:

Column 12, lines 64-66, the structure which reads:

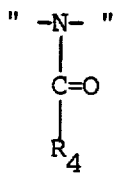

should read:

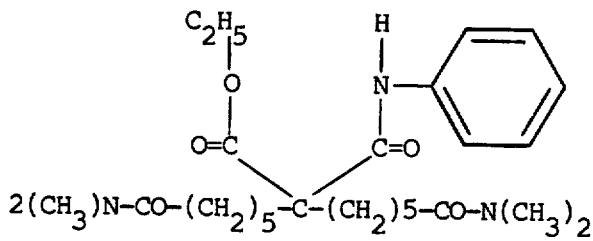

Column 16, line 12, "initiated with: cells" should read —initiated with cells—.

Column 16, line 17, "benzidine reactively" should read —benzidine reactivity—.

Column 19, line 25, after "solution of" and before "1,4-dioxane," should read —19.8 gm commercial bis-hexamethlenetriamine in 500 ml of—.

UNITED STATES PATENT AND TRADEMARK OFFICE
CERTIFICATE OF CORRECTION

PATENT NO. : 5,175,191

DATED : December 29, 1992

INVENTOR(S) : Paul A. Marks, et al.

It is certified that error appears in the above-identified patent and that said Letters Patent is hereby corrected as shown below:

Column 19, line 55, after the structure:

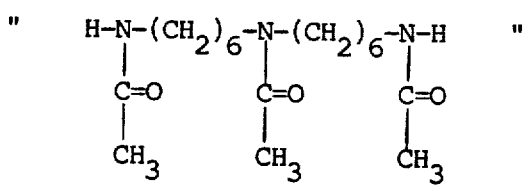

should read --bis-Hexamethylenetriacetamide (IC-135)--.

Column 19, line 66, "with the know" should read --with the the known--.

Column 20, line 24, after "the oily" and before "in ethyl" should read --residue was purified by column chromatography on silica gel--.

Column 20, line 26, "pentylcaboxamide)barbituric acid" should read --pentylcarboxamide)barbituric acid--.

Column 20, line 61, "$^1$H-NMR(CDC13, 200 MHz)" should read --$^1$H-NMR(CDCl$_3$, 200 MHz)--.

Column 20, line 64, "IR(NaCl, CH2Cl2)" should read --IR(NACl, CH$_2$Cl$_2$)--.

Column 20, line 66, "MS glycerol)" should read --MS (FAB, glycerol)--.

Column 20, line 67, "I42" should read --142--.

Column 22, line 42, "for n 2" should read --for n=2--.

UNITED STATES PATENT AND TRADEMARK OFFICE
CERTIFICATE OF CORRECTION

PATENT NO. : 5,175,191

DATED : December 29, 1992

INVENTOR(S) : Paul A. Marks, et al.

It is certified that error appears in the above-identified patent and that said Letters Patent is hereby corrected as shown below:

Column 23, line 4, "38 mmOl" should read 38 mmol--.

Column 24, line 68, after "evaporated" and before " ml)" should read --to a solid residue. The solid was slurried in ether (250--.

Column 27, line 36, "wherein Rl and Rl" should read --wherein Rl and R2--.

Column 28, line 29, "each may is H" should read --each may be H"--.

Column 29, lines 7-13, the structure which reads:

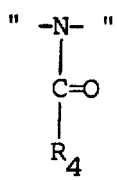

should read:

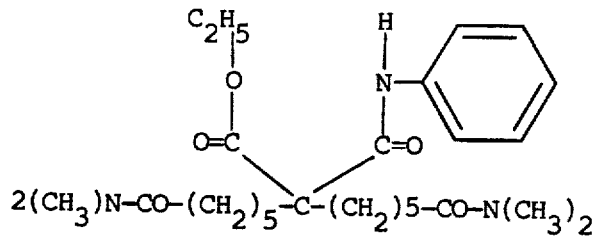

UNITED STATES PATENT AND TRADEMARK OFFICE
CERTIFICATE OF CORRECTION

PATENT NO. : 5,175,191

DATED : December 29, 1992

INVENTOR(S) : Paul A. Marks, et al.

It is certified that error appears in the above-identified patent and that said Letters Patent is hereby corrected as shown below:

Column 29, line 32, "(CDC13, 200 MHz)" should read --(CDCl$_3$, 200 MHz)--.

Column 30, line 25, "HO-N(CH3)-CO-(CH2)6-CO-n(CH3)-OH" should read --HO-N(CH$_3$)-CO-(CH$_2$)$_6$-CO-N(CH$_3$)-OH--.

Column 30, line 45, "2.0 X 10$_6$ cells/ml" should read --2.0 X 10$^6$ cells/ml--.

Column 33, line 19, "2.0 X 10$_6$ cells/ml" should read --2.0 X 10$^6$ cells/ml--.

Signed and Sealed this

Thirty-first Day of May, 1994

Attest:

BRUCE LEHMAN

*Attesting Officer*     *Commissioner of Patents and Trademarks*